United States Patent
Quintero

(10) Patent No.: US 11,679,034 B2
(45) Date of Patent: *Jun. 20, 2023

(54) METHODS AND DEVICES FOR SKIN CLOSURE

(71) Applicant: Ethicon, Inc., Somerville, NJ (US)

(72) Inventor: Julian Quintero, Flemington, NJ (US)

(73) Assignee: Ethicon, Inc., Raritan, NJ (US)

( * ) Notice: Subject to any disclaimer, the term of this patent is extended or adjusted under 35 U.S.C. 154(b) by 319 days.

This patent is subject to a terminal disclaimer.

(21) Appl. No.: 16/907,930

(22) Filed: Jun. 22, 2020

(65) Prior Publication Data

US 2020/0315858 A1 Oct. 8, 2020

Related U.S. Application Data

(63) Continuation of application No. 15/675,159, filed on Aug. 11, 2017, now Pat. No. 10,687,986, which is a (Continued)

(51) Int. Cl.
*A61F 13/00* (2006.01)
*A61F 13/02* (2006.01)
(Continued)

(52) U.S. Cl.
CPC .... *A61F 13/0243* (2013.01); *A61F 13/00085* (2013.01); *A61F 13/024* (2013.01);
(Continued)

(58) Field of Classification Search
CPC ................ A61F 13/024; A61F 13/0243; A61F 13/0253; A61F 13/0259; A61F 13/0263;
(Continued)

(56) References Cited

U.S. PATENT DOCUMENTS 167,162 A 8/1875 French
1,656,199 A 1/1928 Ensley
(Continued)

FOREIGN PATENT DOCUMENTS

AU 2005-215776 A 9/2005
CA 2262408 A 8/2000
(Continued)

OTHER PUBLICATIONS

N/A, "Scar nose & Rinoplasty Surgery—New Gel+Demo: Nose Silicone Gel Sheet (beige)www.newgelplus.com", www.youtube.com, 2012, pp. 1-3, Page Number.
(Continued)

*Primary Examiner* — Kim M Lewis

(57) ABSTRACT

A wound closure device and a method of its use are disclosed. The wound closure device includes a wound closure strip, the wound closure strip including a wound-facing side and a top side, the wound-facing side comprises an adhesive applied over at least a portion of the wound facing side of the wound closure strip and a non-symmetric, two-part release liner assembly detachably adhered to the adhesive, the release liner assembly including a first section and a second section with the second section including a wound closure strip-free portion forming a tab. In an alternate embodiment, the device is multi-segmented and the wound closure strip may be coextensive with the release liner assembly.

17 Claims, 18 Drawing Sheets

Related U.S. Application Data continuation-in-part of application No. 15/280,303, filed on Sep. 29, 2016, now Pat. No. 10,470,934.

(51) Int. Cl.
*A61L 15/58* (2006.01)
*A61L 15/22* (2006.01)
*A61B 17/00* (2006.01)

(52) U.S. Cl.
CPC ...... *A61F 13/0253* (2013.01); *A61F 13/0259* (2013.01); *A61L 15/22* (2013.01); *A61L 15/58* (2013.01); *A61B 17/00491* (2013.01); *A61F 2013/00238* (2013.01); *A61F 2013/00459* (2013.01); *A61F 2013/00817* (2013.01)

(58) Field of Classification Search
CPC .............. A61F 13/0266; A61F 13/0276; A61F 13/0289; A61F 13/00085; A61F 2013/00817; A61F 2013/00238; A61F 2013/00459; A61L 15/22; A61L 15/58; A61B 17/00491
USPC ........................................................ 606/215
See application file for complete search history.

(56) References Cited

U.S. PATENT DOCUMENTS

| | | |
|---|---|---|
| 2,399,545 A | 4/1946 | Davis |
| 2,508,855 A | 5/1950 | Brown |
| 2,721,858 A | 10/1955 | Joyner et al. |
| 2,722,220 A | 11/1955 | Mestrand |
| 2,807,262 A | 9/1957 | Lew |
| 2,905,174 A | 5/1959 | Smith |
| 3,085,572 A | 4/1963 | Blackford |
| 3,254,111 A | 5/1966 | Hawkins et al. |
| 3,402,716 A | 9/1968 | Baxter |
| 3,520,300 A | 7/1970 | Flower, Jr. |
| 3,731,683 A | 5/1973 | Zaffaroni |
| 3,888,247 A | 6/1975 | Stenvall |
| 3,940,362 A | 2/1976 | Overhults |
| 3,983,878 A | 10/1976 | Kawchitch |
| 3,995,641 A | 12/1976 | Kronenthal et al. |
| 4,068,664 A | 1/1978 | Sharp et al. |
| 4,080,348 A | 3/1978 | Korpman |
| 4,126,130 A | 11/1978 | Cowden et al. |
| 4,140,115 A | 2/1979 | Schonfeld |
| 4,263,906 A | 4/1981 | Finley |
| 4,313,865 A | 2/1982 | Teramoto et al. |
| 4,340,043 A | 7/1982 | Seymour |
| 4,364,876 A | 12/1982 | Kimura et al. |
| 4,390,519 A | 6/1983 | Sawyer |
| 4,460,369 A | 7/1984 | Seymour |
| 4,560,723 A | 12/1985 | Millet et al. |
| 4,584,355 A | 4/1986 | Blizzard et al. |
| 4,585,836 A | 4/1986 | Homan et al. |
| 4,591,622 A | 5/1986 | Blizzard et al. |
| 4,612,230 A | 9/1986 | Liland et al. |
| 4,614,183 A | 9/1986 | McCracken et al. |
| 4,630,603 A | 12/1986 | Greenway |
| 4,655,767 A | 4/1987 | Woodard et al. |
| 4,671,266 A | 6/1987 | Legnyel et al. |
| 4,720,513 A | 1/1988 | Kameyama et al. |
| 4,728,380 A | 3/1988 | Jones et al. |
| 4,733,659 A | 3/1988 | Edenbaum et al. |
| 4,767,401 A | 8/1988 | Seiderman |
| 4,793,887 A | 12/1988 | Card et al. |
| 4,793,888 A | 12/1988 | Card et al. |
| 4,795,435 A | 1/1989 | Steer et al. |
| 4,852,571 A | 8/1989 | Gadsby et al. |
| 4,867,747 A | 9/1989 | Yarger |
| 4,872,450 A | 10/1989 | Austad |
| 4,950,282 A | 8/1990 | Beisang et al. |
| 4,966,605 A | 10/1990 | Thieler |
| 4,999,235 A | 3/1991 | Lunn et al. |
| 5,035,687 A | 7/1991 | Sandbank |
| 5,059,424 A | 10/1991 | Cartmell et al. |
| 5,086,763 A | 2/1992 | Hathman |
| 5,088,483 A | 2/1992 | Heinecke |
| 5,106,362 A | 4/1992 | Gilman |
| 5,125,907 A | 6/1992 | Philpott |
| 5,164,444 A | 11/1992 | Bernard |
| 5,173,302 A | 12/1992 | Holmblad et al. |
| 5,232,958 A | 8/1993 | Mallya et al. |
| 5,254,132 A | 10/1993 | Barley et al. |
| 5,259,835 A | 11/1993 | Clark et al. |
| 5,266,371 A | 11/1993 | Sugii et al. |
| D347,059 S | 5/1994 | Mota |
| 5,308,313 A | 5/1994 | Karami et al. |
| 5,328,687 A | 7/1994 | Leung et al. |
| 5,336,209 A | 8/1994 | Porzilli |
| 5,415,626 A | 5/1995 | Goodman et al. |
| 5,429,592 A | 7/1995 | Jensen |
| 5,445,597 A | 8/1995 | Clark et al. |
| 5,449,340 A | 9/1995 | Tollini |
| D363,126 S | 10/1995 | Dusek |
| 5,456,660 A | 10/1995 | Reich et al. |
| 5,476,440 A | 12/1995 | Edenbaum |
| 5,486,547 A | 1/1996 | Matsuda et al. |
| D370,258 S | 5/1996 | Newman |
| D373,750 S | 9/1996 | Gunderson |
| 5,571,079 A | 11/1996 | Bello et al. |
| 5,575,997 A | 11/1996 | Leung et al. |
| 5,582,834 A | 12/1996 | Leung et al. |
| 5,599,858 A | 2/1997 | Buchanan et al. |
| 5,620,702 A | 4/1997 | Podell et al. |
| 5,623,011 A | 4/1997 | Bernard |
| 5,624,669 A | 4/1997 | Leung et al. |
| D382,343 S | 8/1997 | Wandell et al. |
| 5,653,769 A | 8/1997 | Barley, Jr. et al. |
| D383,211 S | 9/1997 | Dunshee et al. |
| 5,662,599 A | 9/1997 | Reich et al. |
| D387,169 S | 12/1997 | Dunshee et al. |
| D389,244 S | 1/1998 | Dunshee et al. |
| 5,705,551 A | 1/1998 | Sasaki et al. |
| D391,639 S | 3/1998 | Dunshee et al. |
| 5,749,895 A | 5/1998 | Sawyer et al. |
| 5,762,955 A | 6/1998 | Smith |
| 5,780,048 A | 7/1998 | Lee |
| 5,782,788 A | 7/1998 | Widemire |
| 5,823,983 A | 10/1998 | Rosofsky et al. |
| 5,823,986 A | 10/1998 | Peterson |
| D402,371 S | 12/1998 | Haynes et al. |
| D403,425 S | 12/1998 | Hinds et al. |
| D404,139 S | 1/1999 | Young |
| 5,861,348 A | 1/1999 | Kase |
| 5,876,745 A | 3/1999 | Muraoka et al. |
| 5,902,443 A | 5/1999 | Kanakubo et al. |
| 5,928,611 A | 7/1999 | Leung |
| 5,931,800 A | 8/1999 | Rasmussen et al. |
| 5,947,917 A | 9/1999 | Carté et al. |
| 5,951,505 A | 9/1999 | Gilman et al. |
| 5,998,694 A | 12/1999 | Jensen et al. |
| D424,699 S | 5/2000 | Allen |
| 6,093,465 A * | 7/2000 | Gilchrist ............... A61F 13/023 602/41 |
| 6,125,265 A | 9/2000 | Yamamoto et al. |
| 6,140,548 A | 10/2000 | Hansen et al. |
| 6,143,352 A | 11/2000 | Clark et al. |
| 6,155,265 A | 12/2000 | Hammerslag |
| 6,183,593 B1 | 2/2001 | Narang et al. |
| D439,973 S | 4/2001 | Choksi |
| 6,217,603 B1 | 4/2001 | Clark et al. |
| 6,238,692 B1 | 5/2001 | Smith |
| 6,245,960 B1 | 6/2001 | Eaton |
| 6,284,941 B1 | 9/2001 | Cox et al. |
| 6,310,166 B1 | 10/2001 | Hickey et al. |
| 6,329,564 B1 | 12/2001 | Lebner |
| 6,352,704 B1 | 3/2002 | Nicholson et al. |
| D458,687 S | 6/2002 | Dale et al. |
| 6,410,818 B1 | 6/2002 | Oyaski |
| 6,439,789 B1 | 8/2002 | Balance et al. |
| D463,564 S | 9/2002 | Siegwart et al. |

(56) References Cited

U.S. PATENT DOCUMENTS

| | | |
|---|---|---|
| 6,455,064 B1 | 9/2002 | Narang et al. |
| 6,479,725 B1 | 11/2002 | Brothers |
| 6,482,431 B2 | 11/2002 | Smith |
| 6,512,023 B1 | 1/2003 | Malofsky et al. |
| D471,984 S | 3/2003 | Dunshee et al. |
| D472,319 S | 3/2003 | Oltmann |
| 6,559,350 B1 | 5/2003 | Tetreault et al. |
| 6,579,469 B1 | 6/2003 | Nicholson et al. |
| 6,582,713 B2 | 6/2003 | Newell et al. |
| D477,076 S | 7/2003 | Wall |
| 6,589,269 B2 | 7/2003 | Zhu et al. |
| 6,595,940 B1 | 7/2003 | D'Alessio et al. |
| 6,596,917 B2 | 7/2003 | Oyaski |
| 6,599,318 B1 | 7/2003 | Gabbay |
| 6,620,846 B1 | 9/2003 | Jonn et al. |
| D480,879 S | 10/2003 | Boehm et al. |
| 6,632,450 B1 | 10/2003 | Gregory |
| 6,635,272 B2 | 10/2003 | Leaderman |
| 6,652,559 B1 | 11/2003 | Tetreault et al. |
| 6,667,051 B1 | 12/2003 | Gregory |
| 6,712,839 B1 | 3/2004 | Lönne |
| 6,787,682 B2 | 9/2004 | Gilman |
| 6,837,027 B2 | 1/2005 | Hickey |
| 6,841,716 B1 | 1/2005 | Tsutsumi |
| 6,942,683 B2 | 9/2005 | Dunshee |
| D515,701 S | 2/2006 | Horhota et al. |
| D516,728 S | 3/2006 | Wall |
| D520,639 S | 5/2006 | Dodd et al. |
| 7,041,124 B2 | 5/2006 | Purcell |
| 7,044,982 B2 | 5/2006 | Milbocker |
| 7,066,934 B2 | 6/2006 | Kirsch |
| 7,122,712 B2 | 10/2006 | Lutri et al. |
| 7,144,390 B1 | 12/2006 | Hannigan et al. |
| 7,164,054 B2 | 1/2007 | Mori et al. |
| D548,348 S | 8/2007 | Nash |
| 7,252,837 B2 | 8/2007 | Guo et al. |
| D562,461 S | 2/2008 | Nash et al. |
| 7,371,400 B2 | 5/2008 | Borenstein et al. |
| D574,962 S | 8/2008 | Atkins et al. |
| D580,553 S | 11/2008 | Nash |
| D581,467 S | 11/2008 | Winningham et al. |
| 7,457,667 B2 | 11/2008 | Skiba |
| D582,561 S | 12/2008 | Sachi |
| D584,415 S | 1/2009 | Sachi |
| 7,576,257 B2 | 8/2009 | LaGreca, Sr. |
| D611,156 S | 3/2010 | Dunshee |
| 7,713,463 B1 | 5/2010 | Reah et al. |
| D618,810 S | 6/2010 | Tanigawa et al. |
| D621,052 S | 8/2010 | Kase |
| D621,053 S | 8/2010 | Kase |
| D624,190 S | 9/2010 | Neri |
| D632,398 S | 2/2011 | Bray et al. |
| D636,881 S | 4/2011 | Clemens et al. |
| 7,943,811 B2 | 5/2011 | Da Silva Macedo, Jr. |
| 7,981,136 B2 | 7/2011 | Weiser |
| 7,982,087 B2 | 7/2011 | Greener et al. |
| D646,789 S | 10/2011 | Barth |
| 8,343,606 B2 | 1/2013 | Marchitto et al. |
| 8,353,966 B2 | 1/2013 | Day et al. |
| D676,490 S | 2/2013 | Bratter et al. |
| 8,372,051 B2 | 2/2013 | Scholz et al. |
| D679,098 S | 4/2013 | Ogawa |
| D679,402 S | 4/2013 | Conrad-Vlasak et al. |
| D679,403 S | 4/2013 | Heinecke et al. |
| D679,405 S | 4/2013 | Arbesman |
| D679,819 S | 4/2013 | Peron |
| D679,820 S | 4/2013 | Peron |
| D685,484 S | 7/2013 | Brambilla |
| 8,528,730 B2 | 9/2013 | Grossman |
| D691,730 S | 10/2013 | Smith et al. |
| D692,566 S | 10/2013 | Adoni |
| D693,010 S | 11/2013 | Mosa et al. |
| D694,892 S | 12/2013 | Chan et al. |
| 8,603,053 B2 | 12/2013 | Riesinger |
| D697,216 S | 1/2014 | Chan et al. |
| 8,642,831 B2 | 2/2014 | Larsen et al. |
| 8,663,171 B2 | 3/2014 | Tambourgi et al. |
| D705,429 S | 5/2014 | Cheney et al. |
| D707,829 S | 6/2014 | Chan et al. |
| D708,751 S | 7/2014 | Chan et al. |
| 8,777,986 B2 | 7/2014 | Straehnz et al. |
| D712,045 S | 8/2014 | Thornton |
| D713,534 S | 9/2014 | Manley, Jr. |
| D713,967 S | 9/2014 | Adoni |
| D714,575 S | 10/2014 | Mah |
| 8,884,094 B2 | 11/2014 | Lockwood et al. |
| D718,812 S | 12/2014 | Sukhbaatar |
| 9,000,251 B2 | 4/2015 | Murphy et al. |
| RE45,510 E | 5/2015 | Hisamitsu |
| D728,803 S | 5/2015 | Sinda et al. |
| D745,688 S | 12/2015 | Chan et al. |
| D745,689 S | 12/2015 | Chan et al. |
| D746,479 S | 12/2015 | Arefieg |
| RE45,864 E | 1/2016 | Peron |
| D746,996 S | 1/2016 | Karlsson et al. |
| D750,789 S | 3/2016 | Mackay et al. |
| D757,950 S | 5/2016 | Karlsson et al. |
| 9,339,417 B2 | 5/2016 | Ogawa |
| 9,381,284 B2 | 7/2016 | Cornet et al. |
| 9,440,010 B2 | 9/2016 | Locke |
| 9,492,171 B2 | 11/2016 | Patenaude |
| 9,623,142 B2 | 4/2017 | Jonn et al. |
| D786,350 S | 5/2017 | Nakai et al. |
| D786,351 S | 5/2017 | Nakai et al. |
| D786,352 S | 5/2017 | Nakai et al. |
| D786,353 S | 5/2017 | Nakai et al. |
| D786,972 S | 5/2017 | Nakai et al. |
| 9,655,622 B2 | 5/2017 | Jonn et al. |
| D790,071 S | 6/2017 | Ahsani |
| D824,525 S | 7/2018 | Lacy et al. |
| D833,526 S | 11/2018 | Nakai et al. |
| 10,434,211 B2 | 10/2019 | Jonn et al. |
| 10,470,935 B2 | 11/2019 | Quintero |
| 10,687,986 B2 * | 6/2020 | Quintero ............ A61L 15/58 |
| 2001/0002432 A1 | 5/2001 | Bugge |
| 2001/0028943 A1 | 10/2001 | Mashiko et al. |
| 2001/0037077 A1 | 11/2001 | Wiemken |
| 2002/0018689 A1 | 2/2002 | Badejo et al. |
| 2002/0019652 A1 | 2/2002 | DaSilva et al. |
| 2002/0037310 A1 | 3/2002 | Jonn et al. |
| 2002/0039867 A1 | 4/2002 | Curro et al. |
| 2002/0049503 A1 | 4/2002 | Milbocker |
| 2002/0185396 A1 | 12/2002 | Mainwaring et al. |
| 2002/0192107 A1 | 12/2002 | Hickey |
| 2002/0193721 A1 | 12/2002 | Vandruff |
| 2003/0031499 A1 | 2/2003 | Heard et al. |
| 2003/0050590 A1 | 3/2003 | Kirsch |
| 2003/0093024 A1 | 5/2003 | Falleiros et al. |
| 2003/0100955 A1 | 5/2003 | Greenawalt et al. |
| 2003/0109819 A1 | 6/2003 | Tsuruda et al. |
| 2003/0125654 A1 | 7/2003 | Malik |
| 2003/0175824 A1 | 9/2003 | Pishko et al. |
| 2003/0220596 A1 | 11/2003 | Dunshee |
| 2003/0225355 A1 | 12/2003 | Butler |
| 2004/0001879 A1 | 1/2004 | Guo et al. |
| 2004/0060867 A1 | 4/2004 | Kriksunov et al. |
| 2004/0106888 A1 | 6/2004 | Lutri et al. |
| 2004/0120849 A1 | 6/2004 | Stewart et al. |
| 2004/0142041 A1 | 7/2004 | MacDonald et al. |
| 2004/0162512 A1 | 8/2004 | Liedtke et al. |
| 2004/0220505 A1 | 11/2004 | Worthley |
| 2005/0015036 A1 | 1/2005 | Lutri et al. |
| 2005/0043820 A1 | 2/2005 | Browning |
| 2005/0085757 A1 | 4/2005 | Santanello |
| 2005/0147457 A1 | 7/2005 | Badejo et al. |
| 2005/0153090 A1 | 7/2005 | Marchitto et al. |
| 2005/0154340 A1 | 7/2005 | Schlussel |
| 2005/0182443 A1 * | 8/2005 | Jonn ............ A61B 17/00491 606/213 |
| 2005/0208100 A1 | 9/2005 | Weber et al. |
| 2005/0288706 A1 | 12/2005 | Widomski et al. |
| 2006/0009099 A1 | 1/2006 | Jonn et al. |
| 2006/0058721 A1 | 3/2006 | Lebner et al. |
| 2006/0141012 A1 | 6/2006 | Gingras |

(56) References Cited

U.S. PATENT DOCUMENTS

| | | |
|---|---|---|
| 2006/0173394 A1 | 8/2006 | Stroock et al. |
| 2006/0265005 A1 | 11/2006 | Beese |
| 2007/0106195 A1 | 5/2007 | Marcoux et al. |
| 2007/0218101 A1 | 9/2007 | Johnson et al. |
| 2007/0272211 A1 | 11/2007 | Kassner |
| 2007/0282238 A1 | 12/2007 | Madsen et al. |
| 2007/0299542 A1 | 12/2007 | Mathisen et al. |
| 2008/0051687 A1 | 2/2008 | Rogers |
| 2008/0154168 A1 | 2/2008 | Lutri |
| 2008/0086113 A1 | 4/2008 | Tenney et al. |
| 2008/0109034 A1 | 5/2008 | Mather et al. |
| 2008/0110961 A1 | 5/2008 | Voegele et al. |
| 2008/0167633 A1 | 7/2008 | Vannucci |
| 2008/0228219 A1 | 9/2008 | Weiser |
| 2008/0228220 A1 | 9/2008 | Weiser |
| 2008/0280037 A1 | 11/2008 | Sheridan et al. |
| 2008/0302487 A1 | 12/2008 | Goodman et al. |
| 2009/0074842 A1 | 3/2009 | Hsu |
| 2010/0106120 A1 | 4/2010 | Holm |
| 2010/0198161 A1 | 8/2010 | Propp |
| 2010/0262091 A1 | 10/2010 | Larsson |
| 2010/0298791 A1 | 11/2010 | Jones et al. |
| 2011/0047766 A1 | 3/2011 | McAulay et al. |
| 2011/0071415 A1 | 3/2011 | Karwoski et al. |
| 2011/0092874 A1 | 4/2011 | Baschnagel |
| 2011/0130699 A1 | 6/2011 | Madsen et al. |
| 2011/0208102 A1 | 8/2011 | Chawki |
| 2011/0253303 A1 | 10/2011 | Miyachi et al. |
| 2012/0052230 A1 | 3/2012 | Olsson et al. |
| 2012/0220912 A1 | 8/2012 | Shang |
| 2012/0238933 A1 | 9/2012 | Murphy et al. |
| 2012/0277645 A1 | 11/2012 | Kikuta et al. |
| 2013/0012988 A1 | 1/2013 | Blume et al. |
| 2013/0041337 A1 | 2/2013 | Aali et al. |
| 2013/0066365 A1 | 3/2013 | Belson et al. |
| 2013/0084323 A1 | 4/2013 | Riebman et al. |
| 2013/0138068 A1 | 5/2013 | Hu et al. |
| 2013/0143326 A1 | 6/2013 | Tai et al. |
| 2013/0144399 A1 | 6/2013 | Tai et al. |
| 2013/0204077 A1 | 8/2013 | Nagale et al. |
| 2013/0218125 A1 | 8/2013 | Stopek et al. |
| 2013/0245784 A1 | 9/2013 | Tan et al. |
| 2013/0274717 A1 | 10/2013 | Dunn |
| 2013/0282049 A1 | 10/2013 | Peterson et al. |
| 2013/0317405 A1 | 11/2013 | Ha et al. |
| 2014/0024989 A1 | 1/2014 | Ueda |
| 2014/0107561 A1 | 4/2014 | Dorian et al. |
| 2014/0121649 A1 | 5/2014 | Calco |
| 2014/0155916 A1 | 6/2014 | Hodgkinson et al. |
| 2014/0171888 A1 | 6/2014 | Croizat et al. |
| 2014/0257348 A1 | 9/2014 | Priewe et al. |
| 2014/0257517 A1 | 9/2014 | Deichmann et al. |
| 2015/0057491 A1 | 2/2015 | Goddard et al. |
| 2015/0209186 A1 | 7/2015 | Abbott et al. |
| 2015/0257938 A1 | 9/2015 | Pensier |
| 2015/0297413 A1 | 10/2015 | Blanco |
| 2015/0314114 A1 | 11/2015 | La Rosa |
| 2015/0351767 A1 | 12/2015 | Zoll et al. |
| 2016/0030248 A1 | 2/2016 | Potters |
| 2016/0089145 A1 | 3/2016 | Quintero et al. |
| 2016/0296673 A1 | 10/2016 | Sambusseti |
| 2017/0035422 A1 | 2/2017 | Belson et al. |
| 2017/0056568 A1 | 3/2017 | Shelton, IV et al. |
| 2017/0056569 A1 | 3/2017 | Vendely et al. |
| 2017/0189159 A1 | 7/2017 | Bartee et al. |
| 2017/0273837 A1 | 9/2017 | Brueckner |
| 2017/0367806 A1 | 12/2017 | Gingras et al. |
| 2018/0085103 A1 | 3/2018 | Quintero et al. |
| 2018/0085259 A1 | 3/2018 | Quintero |
| 2018/0085260 A1 | 3/2018 | Quintero |
| 2019/0381207 A1 | 12/2019 | Jonn et al. |

FOREIGN PATENT DOCUMENTS

| | | |
|---|---|---|
| CN | 1697639 A | 11/2005 |
| CN | 201441532 U | 4/2010 |
| CN | 101965169 A | 2/2011 |
| CN | 102755216 A | 10/2012 |
| CN | 102781433 A | 11/2012 |
| CN | 203234898 A | 10/2013 |
| CN | 204766892 U | 11/2015 |
| EP | 0532275 A | 3/1993 |
| EP | 0730874 A | 9/1996 |
| EP | 0746293 A1 | 12/1996 |
| EP | 1161212 A | 8/2000 |
| EP | 2359782 A | 8/2011 |
| EP | 2377498 A | 10/2011 |
| EP | 2731563 A | 5/2014 |
| EP | 2531155 A | 10/2014 |
| EP | 2805698 A | 11/2014 |
| EP | 3574875 A1 | 12/2019 |
| FR | 2553995 A1 * | 5/1985 |
| GB | 2078763 A | 1/1982 |
| JP | 59-500046 A | 1/1984 |
| JP | 61-203020 A | 12/1986 |
| JP | 62-87624 A | 6/1987 |
| JP | 01-265967 A | 10/1988 |
| JP | 2-140948 A | 11/1990 |
| JP | 3-56429 U | 5/1991 |
| JP | 06-509966 A | 11/1994 |
| JP | 7-016258 A | 1/1995 |
| JP | 2001-265967 A | 9/2001 |
| JP | 1130927 S | 11/2001 |
| JP | 2002-512980 A | 5/2002 |
| JP | 2002-521139 A | 7/2002 |
| JP | 2002-537068 A | 11/2002 |
| JP | 2003-052741 A | 2/2003 |
| JP | 2003-153949 A | 5/2003 |
| JP | 58-124123 U | 1/2004 |
| JP | 2004-24905 A | 1/2004 |
| JP | 2006-061263 A | 3/2006 |
| JP | 2006-509966 A | 3/2006 |
| JP | 2007-522882 A | 8/2007 |
| JP | 3147394 U | 12/2008 |
| JP | 2009-022730 A | 2/2009 |
| JP | 1359502 S | 5/2009 |
| JP | 2011-004850 A | 1/2011 |
| JP | 1571238 S | 3/2017 |
| JP | 1629290 | 4/2019 |
| MX | 241113 A | 10/2006 |
| WO | 1983/002586 A | 8/1983 |
| WO | 1993/004650 A | 3/1993 |
| WO | 1995/004511 A | 2/1995 |
| WO | 1996/040797 A | 12/1996 |
| WO | 1998/026719 A | 6/1998 |
| WO | 2000/006213 A | 2/2000 |
| WO | 2000/049983 A | 8/2000 |
| WO | 2003/008002 A | 1/2003 |
| WO | 2004/049987 A | 6/2004 |
| WO | 2005/007020 A | 1/2005 |
| WO | 2005/051259 A | 6/2005 |
| WO | 2005/079674 A | 9/2005 |
| WO | 2006/017109 A | 2/2006 |
| WO | 2008/082444 A | 7/2008 |
| WO | 2009/067062 A | 5/2009 |
| WO | 2010/134873 A | 11/2010 |
| WO | 2011152368 A1 | 12/2011 |
| WO | 2013/009725 A | 1/2013 |
| WO | 2014/083570 A | 6/2014 |
| WO | 2014/195710 A | 12/2014 |
| WO | 2015/135351 A | 9/2015 |

OTHER PUBLICATIONS

N/A, "Silagen Silicone Sheeting Strips Review|the skin spot", www.youtube.com, 2017, pp. 1-3, Page Number.
JP 7040744, 1995, English claims.
JP 3059327, 1991, English claims.
Japanese Office Action dated Feb. 19, 2019 for Design Appln. No. 2018-017274.

(56) References Cited

OTHER PUBLICATIONS

Japanese Office Action dated Feb. 26, 2019 for Patent Appln. No. 515463.
3M™ Steri-Strip Adhesive Closures Product Catalog Brochure, (2011) 4 pages.
3M™ Steri-Strip Adhesive Closures Product Catalog Brochure, (2011) 8 pages.
3M™ Steri-Strip Adhesive Closures Product Catalog Brochure, (2012) 12 pages.
Allen, L.V. Jr et al 'Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.
Ashley et al.: Further studies involving wound closure with a rapidly polymerizing adhesive; *Plastic and Reconstructive Surgery*; Apr. 1963; vol. 31; pp. 333-343.
Ashley et al.: Nonsutured closure of skin lacerations and nonsutured grafting of skin with a rapidly polymerizing adhesive; *Qtrly Bull. Northwestern University (Evanston, Ill.) Medical School*; 1962; vol. 36; pp. 189-194.
Brombeg et al.: Nonsuture fixation of split-thickness skin grafts; *Surgery*, Jun. 1964; vol. 55; pp. 846-853.
Cramer: Rapid Skin Grafting in Small Animals; *Plastic and Reconstructive Surgery and the Transplantation Bull*; Oct. 1962, vol. 30; pp. 149-150.
Cramer et al.: Autograft rejection induced by homografting. A phenomenon intermediate between homograft rejection and autoimmunity; *Plastic and Reconstructive Surgery*; Jun. 1965; vol. 35; pp. 572-587.
DeMaria, E. 'New skin closure system facilitates wound healing after cardiovascular implantable electronic device surgery' World Journal of Clinical Cases (2015) 3(8) pp. 675-677.
Dermabond Prineo Skin Closure Systems (22 cm) Brochure (2014), 7 pages.
Dermabond Prineo Skin Closure Systems (22 cm) Brochure (2015), 2 pages.
Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).
Inou: Studies on the Surgical Use of Plastic Adhesive; *Am. Journal of Proctology*; 1962; vol. 13; pp. 219-226.
Jesse et al.: Fixation of split-thickness skin grafts with adhesive; *Plastic and Reconstructive Surgery*; Mar. 1964; vol. 33; pp. 272-277.
Kaplan: A technique of nonsuture wound closure with a plastic tissue adhesive; *Plastic and Reconstructive Surgery*; Feb. 1966; vol. 37(2); pp. 139-142.
Keddie et al.: Intrafollicular tinea versicolor demonstrated on monomer plastic strips; *Journal of Investigative Dermatology*; Sep. 1963; vol. 41; pp. 103-106.
Lazar, H.L. et al 'Novel Adhesive Skin Closures Improve Wound Healing Following Saphenous Vein Harvesting' J. Card Surg (2008) 23 pp. 152-155.
Leukosan SkinLink Application Guide (2006) 1 page.
Leukosan Skinlink. BSN Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.
Pam Marketing Nut. Yikes! The Social Medica Quick Fix Band-Aids are Falling Off! Jul. 2012 [earliest online date], [site visited May 8, 2018]. Available from Internet, ,URL: http://www.pammarketingnut.com/2012/07/yikes-the-social-media-quick-fix-band-aids-are-falling-off/> (Year: 2012).
Parrish et al.: Synthetic resin adhesive for placement of skin grafts; *American Surgeon*; Nov. 1964; vol. 30; pp. 753-755.
Raekallio et al.: Acute reaction to arterial adhesive in healing skin wounds; *Journal of Surgical Research*; Mar. 1964; vol. 4; pp. 124-127.
Stone: Nonsuture closure of cutaneous lacerations, skin grafting and bowel anastomosis; *American Surgeon*; Mar. 1964; vol. 30; pp. 177-181.
TissuGlu Surgical Adhesive Patient Information Brochure. Cohera Medical, Inc. (2014) 6 pages.
TissuGlu FDA Summary of Safety and Effectiveness Data. Feb. 3, 2014 40 pages.
Topaz, M. et al 'The TopClosure 3S System, for skin stretching and a secure wound closure' Eur J Plast Surg (2012) 35 pp. 533-543.
TopClosure 3S System—Skin Stretching and Secure Wound Closure System Product Information Sheet (2010) 15 pages.
Wang et al 'Biodegradable microfluidic scaffolds for tissue engineering from amino alcohol-based poly(ester amide) elastomers' Organogenesis (2010) 6:4, pp. 212-216.
Wolfe et al.: The application of hydrostatic pressure to the burn injury, an experimental study: *Journal of Trauma: Injury Infections & critical Care*; May 1962; vol. 2; pp. 262-272.
ZipLine medical Zip Surgical Skin Closure Brochure (2013) 4 pages.
Corrected International Search Report International Application No. PCT/US2005/004948 dated Jun. 22, 2005.
Extended European Search Report re: 14166813.7 dated Jul. 7, 2014.
International Preliminary Report on Patentability for International Application No. PCT/US2005/024042 dated Jan. 16, 2007.
International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Supplementary European Search Report for Application No. EP05769387 dated Jul. 9, 2009.
Supplementary European Search Report for Application No. EP05723162 dated Nov. 5, 2009.
Supplementary European Search Report for Application No. EP14166813 dated Jun. 30, 2014.
Written Opinion re: PCT/US2015/051919 dated Apr. 14, 2016.
Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.
Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.

(56) References Cited

OTHER PUBLICATIONS

Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.
Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Office action received from USPTO for co-pending U.S. Appl. No. 12/207,984 dated Aug. 22, 2013.
Office action received from USPTO for co-pending U.S. Appl. No. 12/207,984 dated Dec. 4, 2013.
Office action received from USPTO for co-pending U.S. Appl. No. 12/163,021 dated Jan. 3, 2014.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/278,376 dated Sep. 11, 2018.
Office action received from USPTO for U.S. Appl. No. 15/278,376 dated Feb. 21, 2019.
Office action received from USPTO for U.S. Appl. No. 15/675,159 dated May 14, 2019.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.
U.S. Appl. No. 09/919,877, filed Aug. 2, 2001.
U.S. Appl. No. 10/779,721, filed Feb. 18, 2004.

* cited by examiner

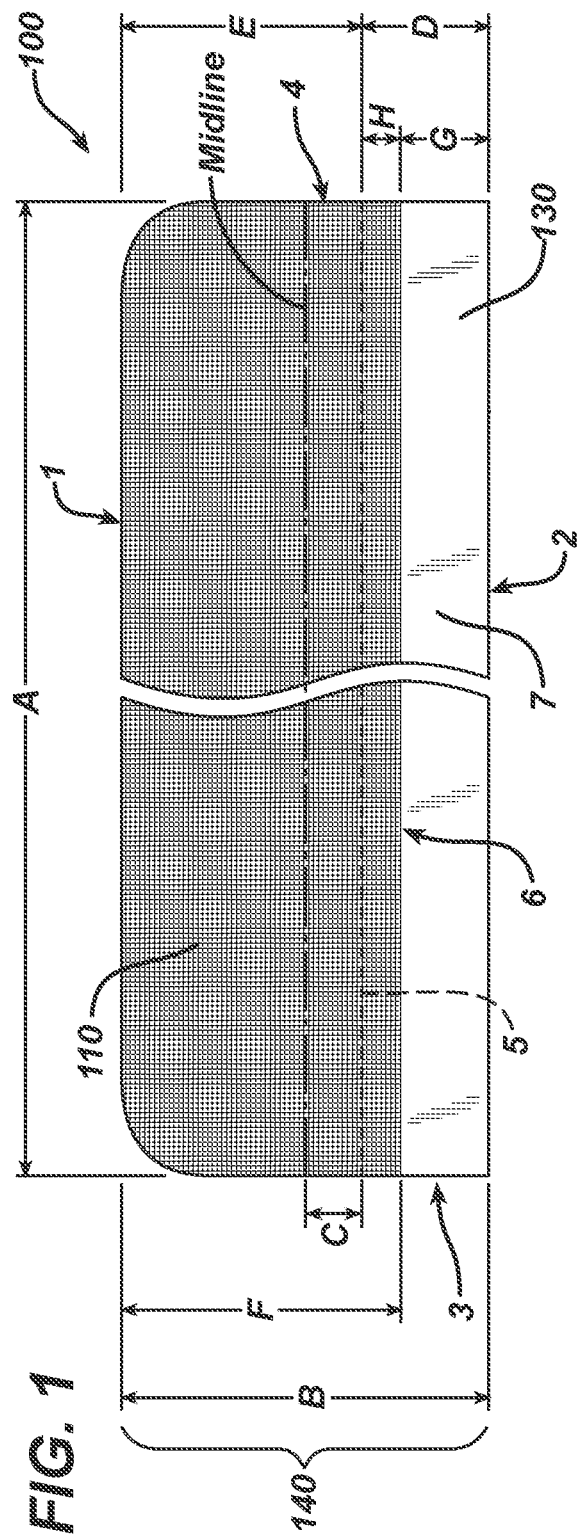
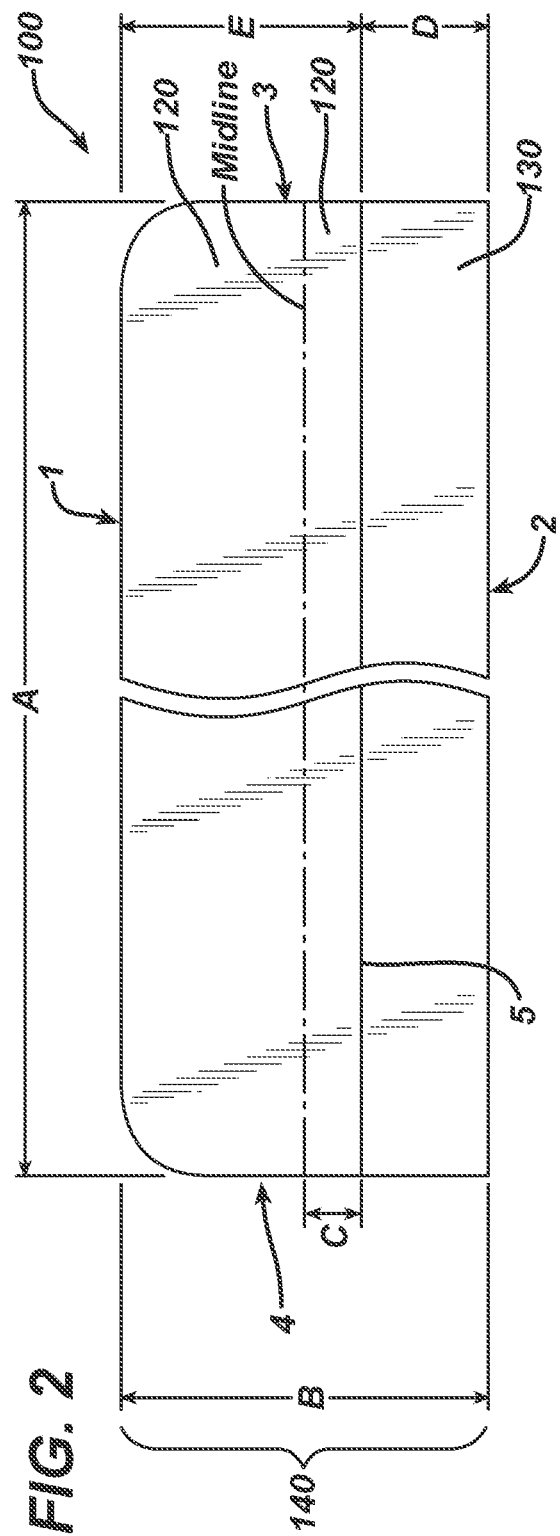
FIG. 1
FIG. 2

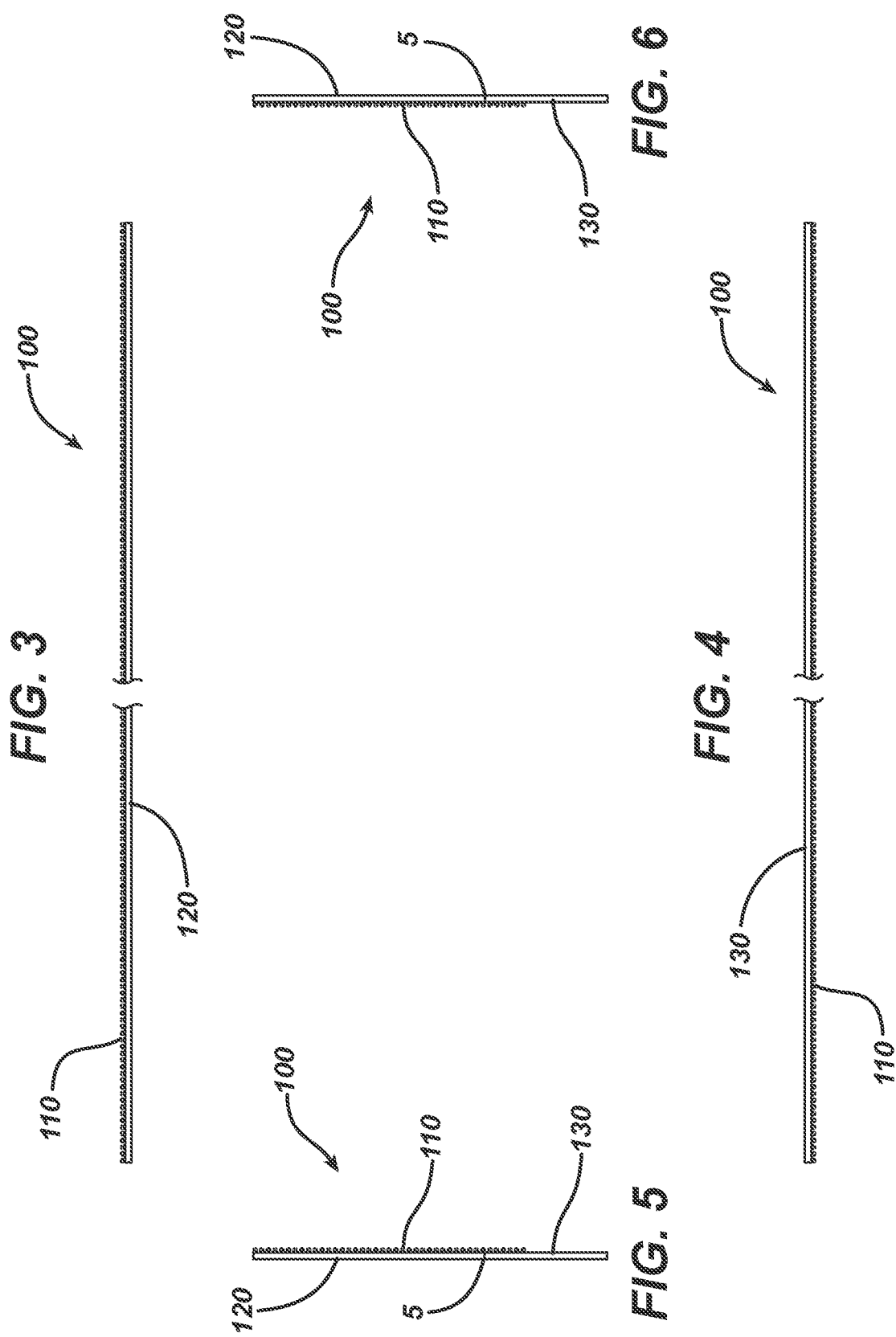

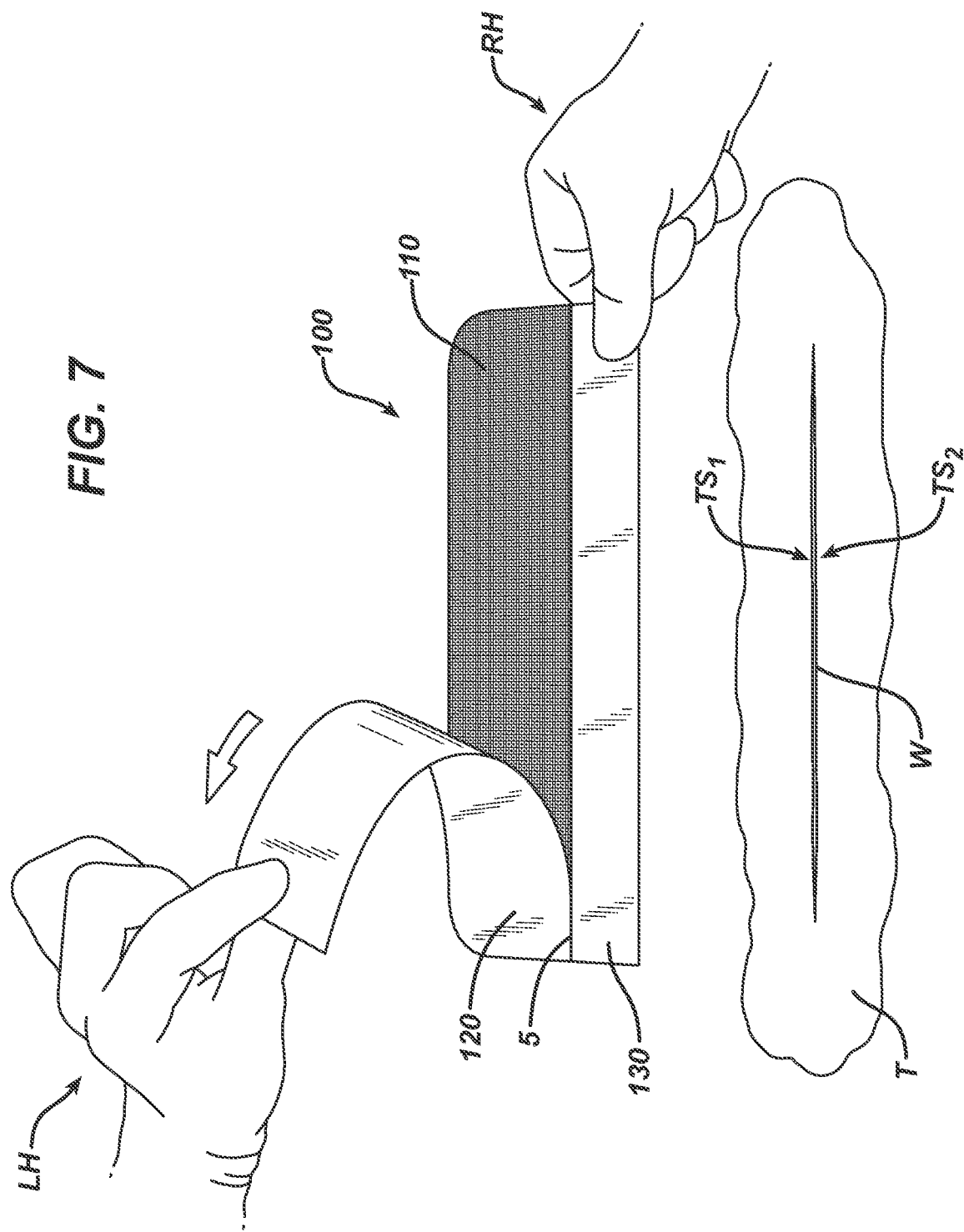

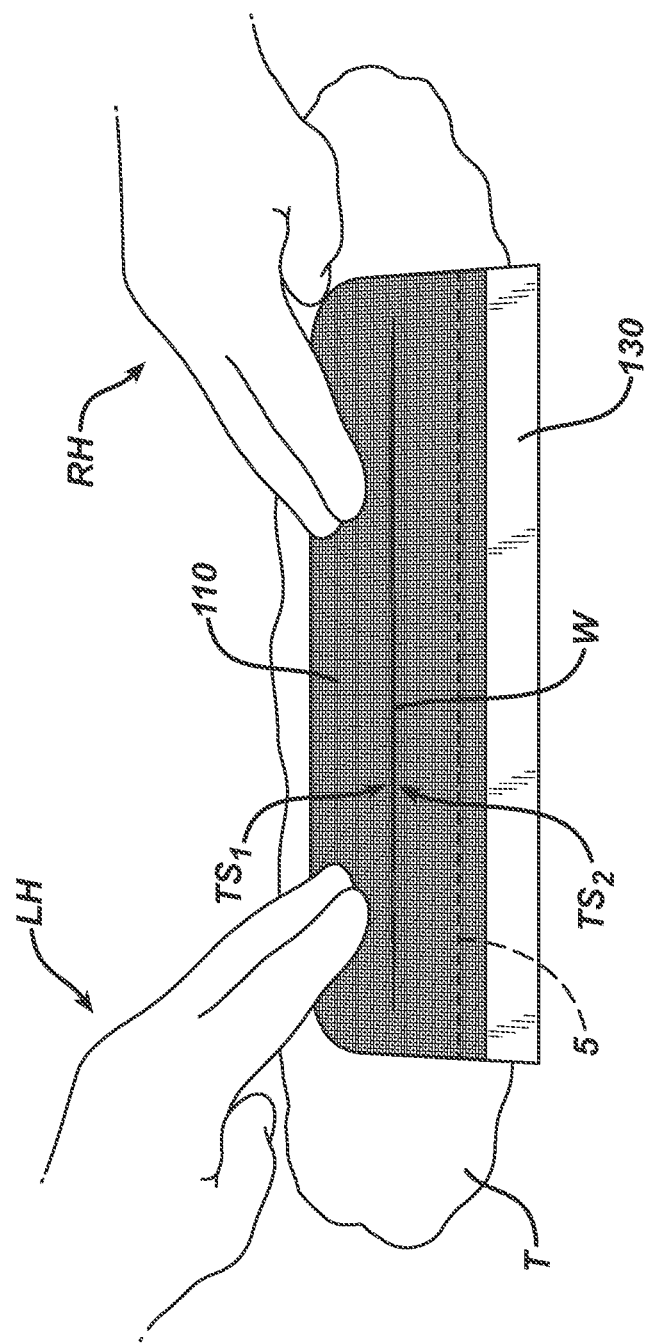

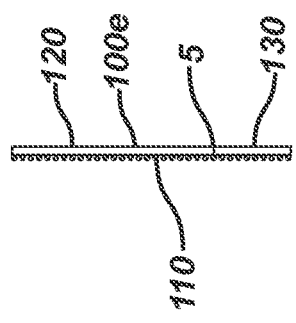
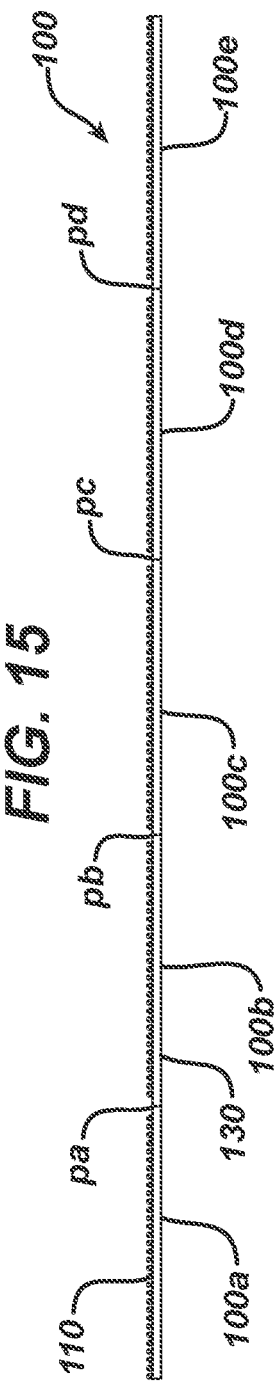
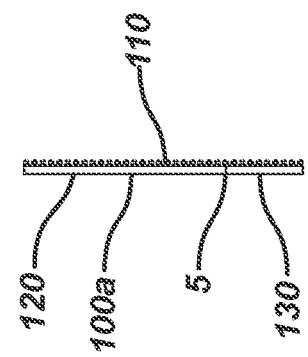
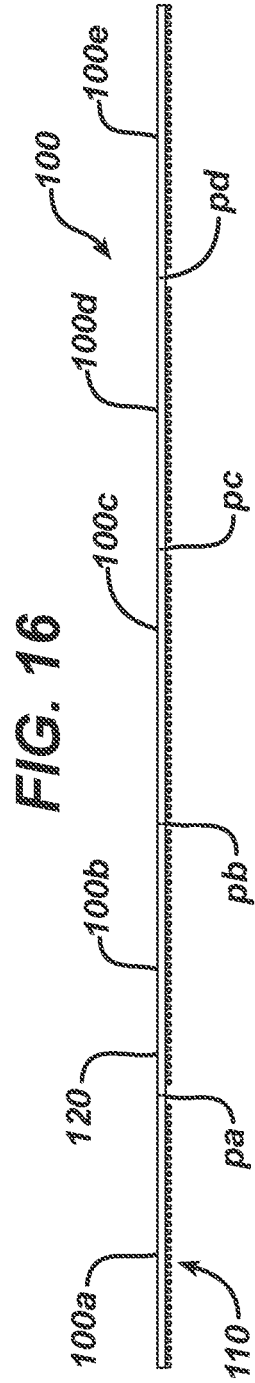

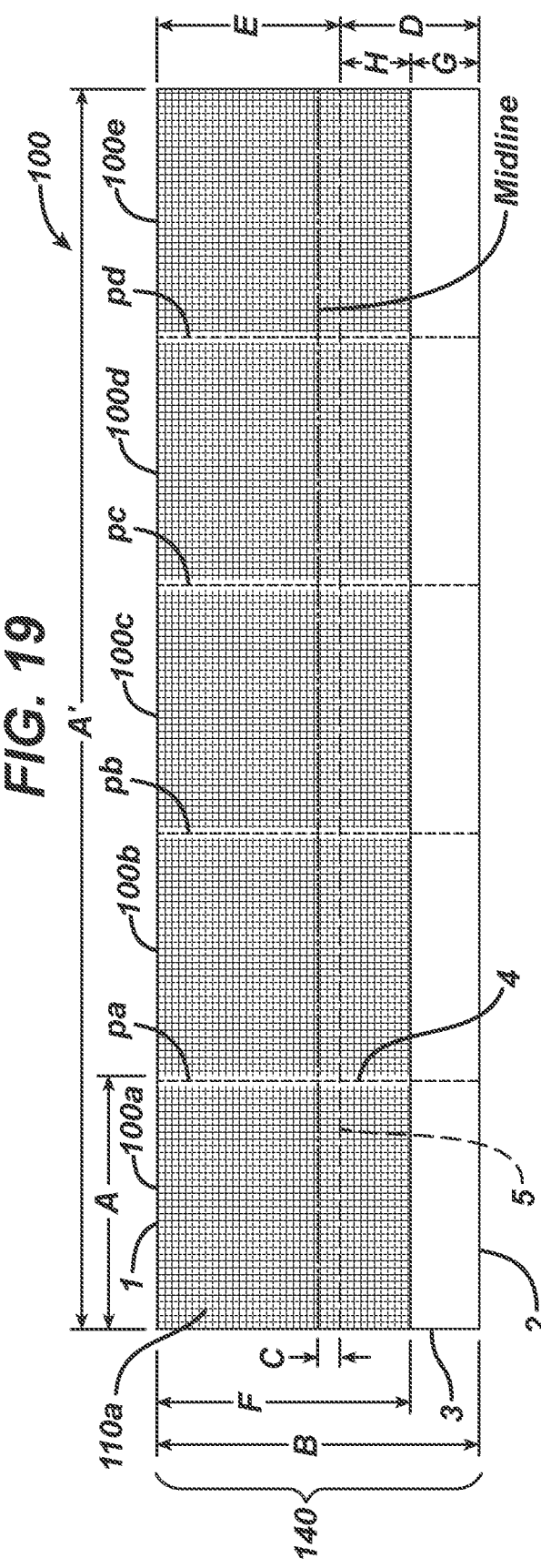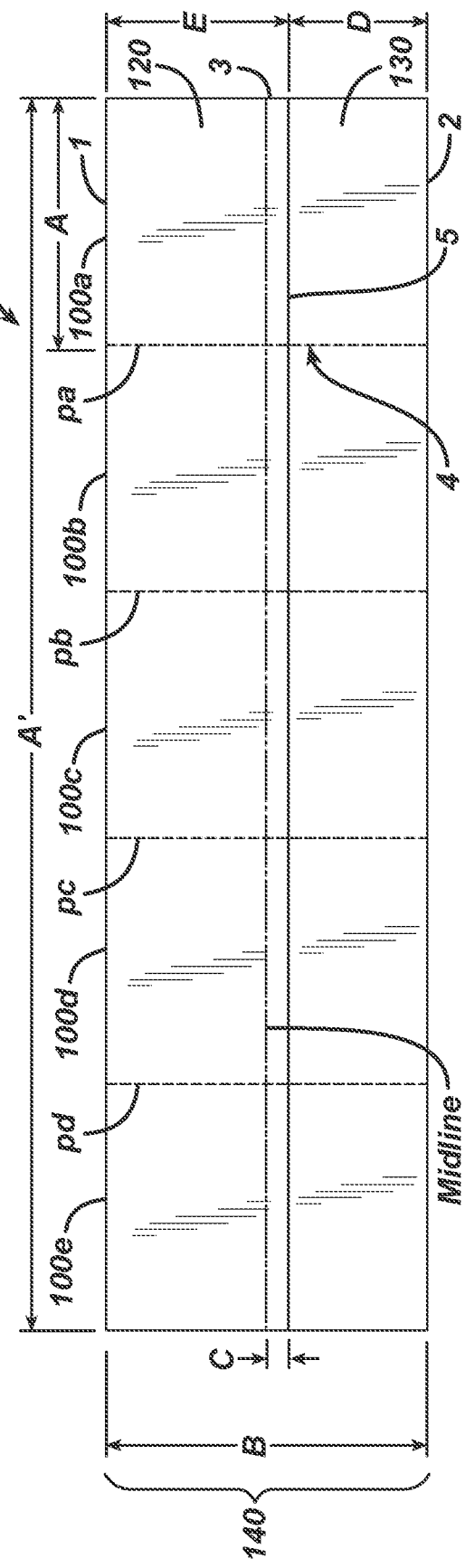

METHODS AND DEVICES FOR SKIN CLOSURE

CROSS REFERENCE TO RELATED APPLICATION

This application is a continuation of U.S. patent application Ser. No. 15/675,159 filed Aug. 11, 2017, which is a continuation-in-part of and claims the benefit of U.S. patent application Ser. No. 15/280,303, filed Sep. 29, 2016, now U.S. Pat. No. 10,470,934. The complete disclosures of the aforementioned related U.S. patent application is hereby incorporated herein by reference for all purposes.

BACKGROUND OF THE INVENTION

1. Field of the Invention

This invention is concerned with devices, systems and methods for wound closure, particularly for skin closure of wounds formed by lacerations or surgical incisions.

2. Related Art

Wound closure tapes and topical adhesives provide an alternative to wound closure by staples and sutures. Among the advantages of using wound closure tapes or topical adhesives, and their combinations include less tissue trauma, improved cosmetic outcomes, and less pain compared with staples and sutures when treating skin closures.

US 2002/0193721 discloses a wound closure grip-like tape apparatus and methods of its use. Reference to FIG. 10 of US 2002/0193721 and the corresponding text of this publication shows how the grip tape is used to secure the wound of FIG. 9. In particular, paragraph 43 of the publication describes three techniques of wound closure reproduced in part as follows: "The first exemplary means of sealing the wound is to place WCGT ("Wound Closure Grid Tape") 100 on one side of the wound 90 with a slight bend along the axis between numbers 92 and 93 such that the other side 91 is tilted above the skin and thus will not adhere. With side 90 pressed in place and with the appropriate pressure applied, the WCGT is tugged with one hand while the other hand (or the thumb of the hand if being self-applied or with one hand) pushes the skin on the other side 91 into position, and then the WCGT is lowered into place. This handling can be done by grasping the WCGT at the edges where denigration of the adhesive is not as critical, or alternately by leaving the backing attached to the secondary side 91 while the first side is pressed into place 90. The second exemplary means to apply is to curve the WCGT upwards, or hold it in a curved position upwards along the longer axis shown, and position it starting at one end of the wound 92. Then, as previously, the wound is pressed together and the WCGT is pressed into place gradually along the length of the wound, going from one end 92 to the other 93. For small wounds, a third approach is to hold the WCGT by the edges and close the wound via pressures outside of the expected WCGT area, and then press the WCGT in place all at once."

In the forgoing description, denigration of the wound-contacting adhesive is a recognized problem since holding at least some of the underside of WCGT 100 is required particularly when side 90 of the wound is drawn toward side 91 of the wound. Thus, from the forgoing description, it appears that wound closure tape only to has a single release liner.

US 2008/0302487 A1 describes a dispensing device configured to operate with an adhesive backed mesh and backing film for tissue bonding. The device prevents or eliminates distortion of the mesh prior to application to the wound sites and includes means for reducing or eliminating binding during use. The dispensing device is configured to operate in a "forward" mode (substrate to which mesh is applied passes beneath applicator after mesh is applied) to provide essentially an unobstructed view of the wound site during use. The backing film is a single strip that protects denigration of adhesive and self adherence of the coiled adhesive-backed mesh.

US 2005/0182443 A is directed to a tissue bonding article which includes a flexible material, an adhesive substance applied over at least a portion of a bottom side of the flexible material, and a polymerizable adhesive composition permeated throughout at least a portion of the flexible material. Although not specifically shown in the figures, a suitable backing or release material may also be used to cover the adhesive substances applied to the bottom side of the flexible material. Such backing materials are well known in the art for covering adhesives and can include, for example, paper, plastic, or the like.

There continues to be a need for improved devices and systems that use surgical tapes, topical adhesives and their combinations such as those provided by this invention.

BRIEF DESCRIPTION OF THE DRAWINGS

FIG. 1 depicts a top view of a wound closure device comprising a non-symmetric, two-part release liner in accordance with an embodiment of the invention.

FIG. 2 depicts a wound-facing view of a wound closure device (prior to removal of the release liners and prior to application to a wound) comprising a non-symmetric, two-part release liner in accordance with an embodiment of the invention.

FIGS. 3-6 depict edge views of a wound closure device comprising a non-symmetric, two-part release liner in accordance with an embodiment of the invention.

FIG. 7 depicts a first step for use of the device in accordance with the invention.

FIG. 8 depicts a second step for use of the device in accordance with the invention.

FIGS. 15-18 depict edge views of the wound closure device of FIGS. 13 and 14 comprising a non-symmetric, two-part release liner in accordance with an embodiment of the invention.

FIG. 19 depicts an alternate embodiment of the invention with the bottom view of a wound closure device (prior to removal of the release liners and prior to application to a wound) comprising a non-symmetric, two-part release liner in accordance with an embodiment of the invention.

FIG. 20 depicts a top view of the wound closure device of FIG. 19 comprising a non-symmetric, two-part release liner in accordance with an embodiment of the invention

SUMMARY OF THE INVENTION

Figure 9:
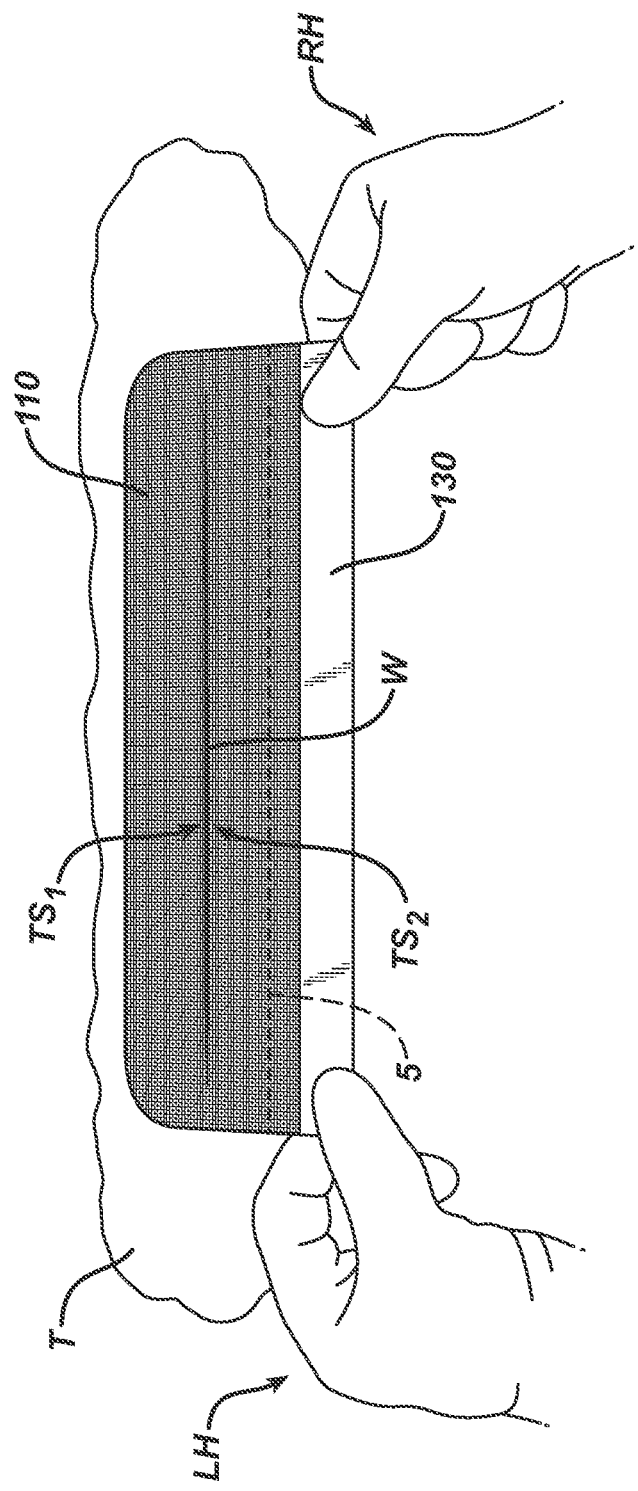
FIG. 9 depicts a third step for use of the device in accordance with the invention.

One aspect of this invention is directed to a wound closure device having a length A, a width B, an upper edge, a lower edge, a right-hand edge, and a left-hand edge comprising:

a wound closure strip having a length A, a width F, a wound-facing side, a top side, an upper edge and a lower edge, the wound-facing side comprising an adhesive applied over at least a portion of the wound facing side;

a release liner assembly detachably adhered to the wound closure strip by the adhesive, the release liner assembly consisting of a first section having a length A and a width E and a second section having a length A and a width D;

wherein the release liner assembly extends the full length A of the wound closure device and extends the full width B of the wound closure device, such that the release liner assembly forms a wound closure strip-free tab, wherein the wound closure strip-free tab has a width of G extending from the lower edge of the wound closure device to the lower edge of the wound closure strip;

wherein the width F of the wound closure strip is greater than the width E of the first section by a width H, where H is equal to length D minus length G; and wherein the first section and the second section are separated from each other by a liner cut.

In a preferred aspect of the invention, the wound closure strip is porous;

the length A is from 2 to 20 cm and the width B from 1.7 to 12 cm;

the wound closure strip has a width F extending from the upper edge of the wound closure device and where F is from 1.5 to 8 cm;

the wound closure strip-free tab has a width G of 0.2 to 4.0 cm;

the first section of the release liner assembly has a width of E extending from the upper edge of the wound closure device and is from 1.5 to 8.0 cm and the second section of the release liner assembly has a width D extending from the lower edge of the wound closure device is from 0.2 to 4 cm such that the width E of the first section is greater than the width D of the second section; and the width B of the device is equal to the width E of the first section plus the width D of the second section.

A further aspect of this invention is directed toward a method of closing a wound having at least a first separated topical tissue surface and a second separated topical tissue surface comprising the steps of:

a) utilizing any one of the embodiments of the inventive wound closure devices described herein and generally comprising a wound closure strip, the wound closure strip comprising a wound facing side and a top side, the wound facing side comprising an adhesive applied over at least a portion of the wound facing side and a non-symmetric, two-part release liner assembly detachably adhered to the adhesive, the release liner assembly comprising a first section and a second section with the second section comprising a wound closure strip-free portion forming a tab;

b) removing the first section of the release liner assembly to expose a portion of the wound facing side of the wound closure strip while grasping the tab of the second section of the release liner assembly;

c) adhering a portion of the exposed wound facing side of the wound closure strip to the at least first separated topical tissue surface and pulling the tab of the second section of the release liner toward the at least second separated topical tissue surface to form two abutted topical tissue surfaces and further adhering the exposed wound facing side of the wound closure strip to the at least second topical tissue surface; and d) removing the second section of the release liner assembly to further expose a wound facing side of the wound closure strip and adhering the further exposed wound closure strip the second topical tissue surface.

The device used in the method of the invention may be any of the devices disclosed herein.

Desirably the method further comprises the step of applying a flowable, polymerizable adhesive over the adhered wound closure strip.

In alternate embodiments, the invention comprises a wound closure device that is multi-segmented and comprising several individual wound closure devices.

Advantages of this invention include:

1) Minimization of adhesive transfer from the product to the user's fingers/gloves, therefore maximizing grip to tissue.

2) Due to the presence of the second section of the release liner, ease of repositioning the wound closure strip once deployed on approximated wound edges.

3) Adhesive is present on only the side that is intended to be in contact with tissue. So there is no accidental adherence of objects to the wound closure strip side not in contact with tissue.

4) Manipulation of the wound closure strip is stable during tissue approximation as the second release paper section provides sufficient rigidity.

DETAILED DESCRIPTION OF PREFERRED EMBODIMENTS OF THE INVENTION

A key aspect for the improved ease of use of wound closure devices of this invention lies in the non-symmetric, two-part release liner assembly used in conjunction with a wound closure strip.

FIGS. 1 and 2 depict a top view and wound-facing view, respectively, of one embodiment of the wound closure device 100 of the present invention having upper edge 1, lower edge 2, right-hand edge 3 and left-hand edge 4. Referring to FIGS. 1 and 2, wound closure device 100 of length A and width B comprises wound closure strip 110 of length A, width F, and lower edge 6; and release liner assembly 140 having a cut 5 and consisting of a first section 120 of length A and width E and second section 130 of length A and width D. It should be noted that dimension C represents the width past the midline of wound closure device 100 that first section 120 extends; dimension H represents the overlap of wound closure strip 110 with second section 130; and dimension G represents the portion 7 of second section 130 that is free of wound closure strip 110 and available for gripping device 100 without having to touch the adhesive containing wound contacting side of wound closure strip 110.

FIGS. 3, 4, 5 and 6 provide an upper edge view, a lower edge view, a left-side edge view and a right-side edge view, respectively, of device 100.

Typical and preferred dimensions for wound closure device 100 are:

| Dimension | Typical(cm) | Most Preferred(cm) |
|---|---|---|
| A | 2.0-20.0 | 12.0 |
| B | 1.0-14 | 4.5 |
| C | >0.0 | 1.0 |
| D | 0.5-4.0 | 1.5 |
| E | 0.6-10.0 | 3.0 |
| F | 1.0-8.0 | 3.5 |
| G | 0.2-4.0 | 1.0 |
| H | 0.2-2 | 0.5 |

With respect to the various dimensions noted above, one skilled in the art would recognize that other dimensions for the wound closure device of this invention are possible depending on the specific dimensions one skilled in the art may select and adapt to treat wounds or incisions of various sizes and shapes. Additionally, for example, referring to FIG. 1, it is envisioned that wound closure strip 110 perimeter p need not be coextensive with portions of device 100 perimeter p', and can be partially coextensive or not be coextensive at all depending if a margin between wound closure strip 110 and release liner assembly 140 is desired.

In general, device 100 may be of any length A and width B that permits the user to effectively apply to close a wound or incision. For many applications, length A will typically range from about 2 cm to about 20 cm, preferably from about 10 cm to about 15 cm, and most preferably about 12 cm. Width B will typically range from about 1.0 cm to about 14 cm, preferably from about 2 to about 10 cm, and most preferably about 4.5 cm.

Additionally, wound closure strip 110 may be of any length A and width F that permits the user to effectively apply to close a wound or incision. For many applications, length A will typically range from about 2 cm to about 20 cm, preferably from about 10 cm to about 15 cm, and most preferably about 12 cm. Width F will typically range from about 1.0 cm to about 8 cm, preferably from about 2 cm to about 6 cm, and most preferably about 3.5 cm.

Dimension C, the distance between the Midline of wound closure device 100 and release liner cut 5 between first section 120 and second section 130. It is dimension C that makes the release assembly a non-symmetric, two-part assembly. If dimension C was equal to 0 cm, then the release assembly would no longer be non-symmetric as then the release assembly cut 5 would be at the Midline and hence the first release section 120 and the second release section 130 would be of equal width. So dimension C should be greater than O and ranges from 0.1 cm to about 2 cm, preferably from about 0.5 cm to about 1.5 cm, and most preferably about 1.0 cm.

Dimension D ranges from 0.5 cm to about 4 cm, preferably from about 0.7 cm to about 3 cm, and most preferably about 1.5 cm. It is within the foregoing ranges that device 100 is conveniently handled with sufficient overlap of wound closure strip 110 and second section 130 to adequately accomplish approximation of the separated topical tissue surface of a wound.

Dimension E is the width of the first section 120 and relates to the width of wound closure strip 110 that is suitable for the user to position and/or reposition wound closure strip 110 for the initial approximation of the separated topical tissue surfaces of a wound. Dimension E ranges from 0.6 cm to about 10 cm, preferably from about 2.0 cm to about 5 cm, and most preferably about 3.0 cm. It is within the foregoing ranges that wound close strip 110 adequately approximates and cover wounds ranging in sizes from 1 cm to about 20 cm.

Dimension G ranges from 0.2 cm to about 4 cm, preferably from about 0.5 cm to about 3 cm, and most preferably about 1.0 cm. It is within the foregoing ranges that device 100 is conveniently handled without denigrating the pressure sensitive adhesive of the wound-face side of wound closure strip 110.

Dimension H ranges from 0.2 cm to about 2.0 cm, preferably from about 0.3 cm to about 1.0 cm, and most preferably about 0.5 cm. It is within the foregoing ranges that device 100 is conveniently handled with sufficient adherence of second section 130 to wound closure strip 110 to accomplish approximation of the wound.

For treatment of surgical wound incisions of about 1.0 cm to about 12 cm, a preferred embodiment of device 100 is for an overall length A of about 12 cm and overall width B of about 4.5 cm, wound closure strip 110 of overall length A of about 12 cm and overall width F of about 3.5 cm, Dimension C of about 1.0 cm, Dimension D of about 1.5 cm, Dimension E of about 3.0 cm, Dimension G of about 1.0 cm and Dimension H of about 0.5 cm.

It would be appreciated by one of skill in the art that device 100 may be cut or trimmed to size for wounds within the above identified range. In practice, it is desirable to have wound closure strip 110 extend approximately at least 0.3 cm, preferably 1 cm from the longitudinal ends of the wound or incision site.

Alternate embodiments of this invention are contemplated wherein the device comprises a wound closure device that is multi-segmented and comprises several individual wound closure devices as shown in FIGS. 12-24. A method of using such devices is shown in FIGS. 25-30.

Figure 12:
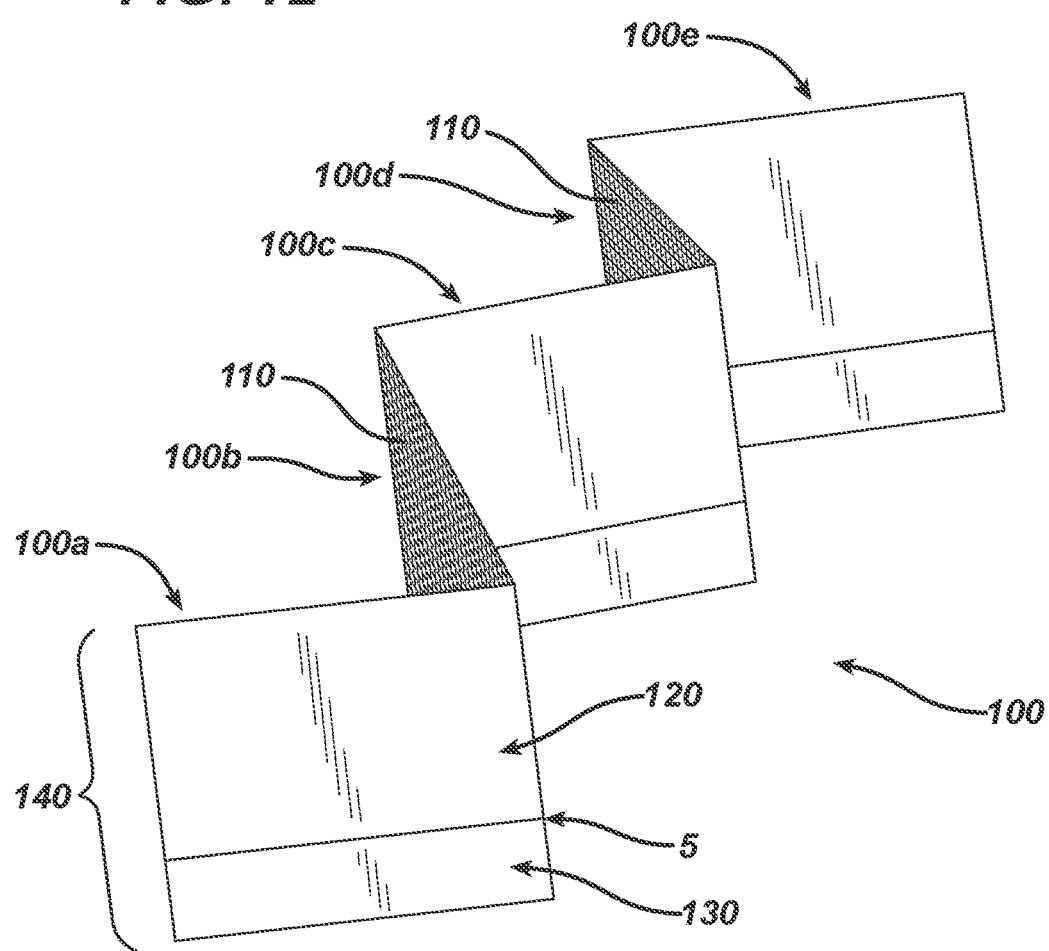
FIG. 12 depicts an alternate embodiment of the device in accordance with the invention which comprises several perforated segments of individual wound closure devices.

Referring to FIG. 12, device 100 comprises wound closure strip 110 and release liner assembly 140 having a first section 120 and a second section 130 separated by cut 5. Device 100 further comprises several perforated segments of individual wound closure devices 100a, 100b, 100c, 100d, and 100e. This embodiment demonstrates the versatility of the invention in being able to provide an array of devices that may be more suitable for the closure of smaller incisions, such as those made in laparoscopic procedures having incisions in the range of 0.5-1.5 cm. Also in this embodiment, wound closure strip 110 is coextensive with release liner assembly 140. An alternative embodiment where wound closure strip 110 is not coextensive with release liner assembly 140 is described below.

Figure 13:
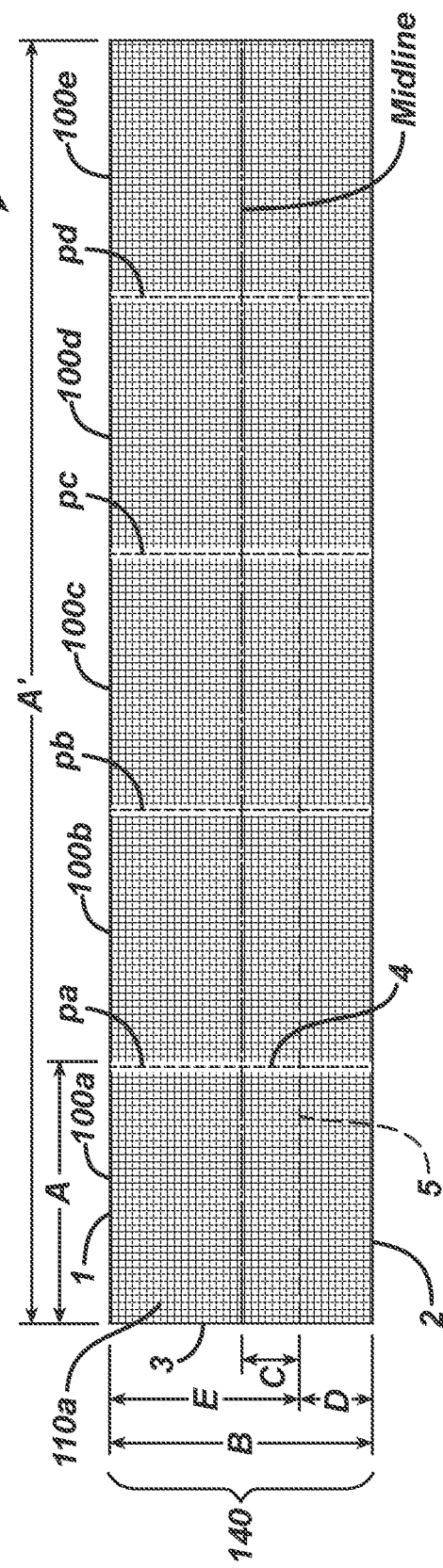
FIG. 13 depicts a bottom view of the wound closure device of FIG. 12 (prior to removal of the release liners and prior to application to a wound) comprising a non-symmetric, two-part release liner in accordance with an embodiment of the invention.

FIG. 13 depicts the bottom view of the wound closure device 100 of FIG. 12 (prior to separation from the multi-segmented array, removal of the release liners and application to a wound) of overall segmented length A' and width B comprising a non-symmetric, two-part release liner. More specifically, segmented devices 110a, 100b, 100c, 100d and 100e are separated by perforations pa, pb, pc, and pd, respectively. Further referring to segmented device 100a, this device of length A and width B comprises top side edge 1, bottom side edge 2, left edge 3 and right edge 4.

Figure 14:
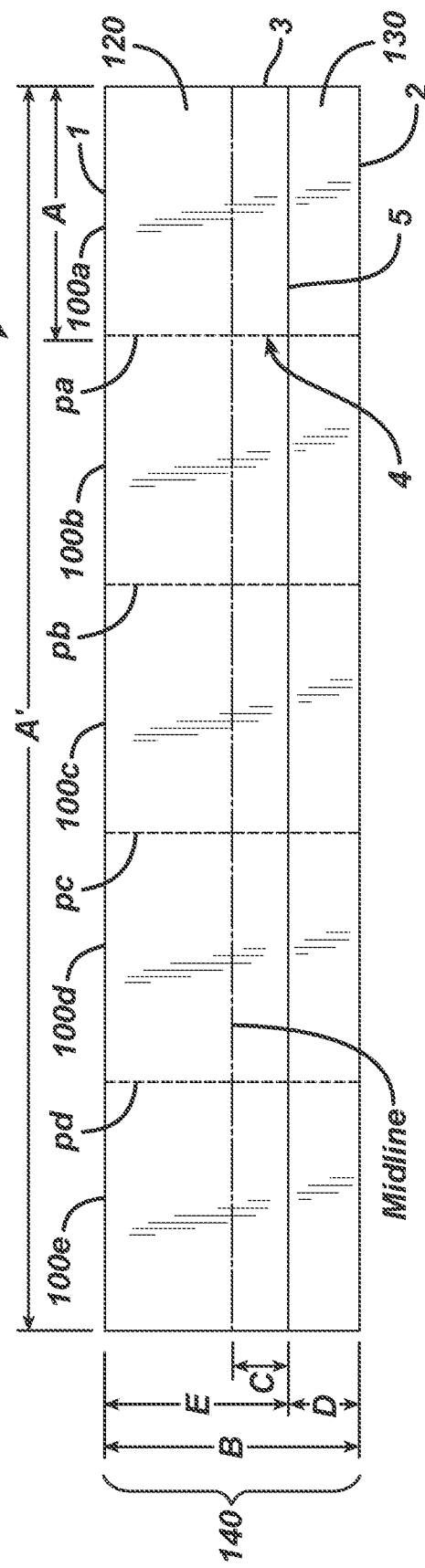
FIG. 14 depicts a top view of the wound closure device of FIG. 12 comprising a non-symmetric, two-part release liner in accordance with an embodiment of the invention
Figure 21:
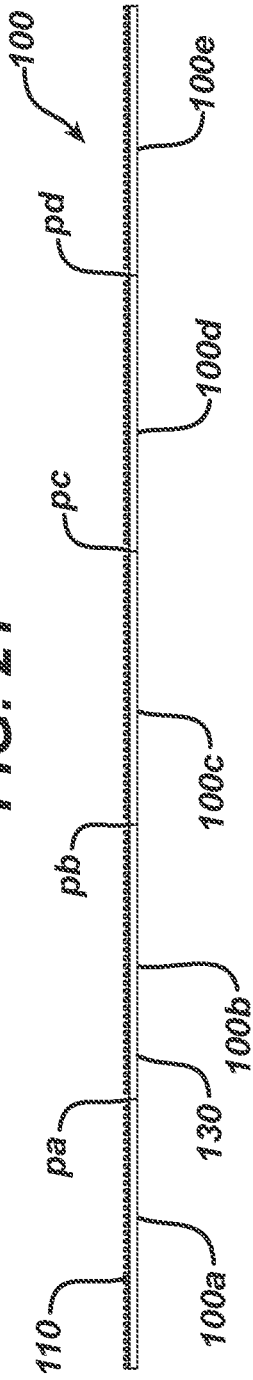
FIGS. 21-24 depict edge views of the wound closure device depicted in FIGS. 19 and 20 comprising a non-symmetric, two-part release liner in accordance with an embodiment of the invention.
Figure 24:
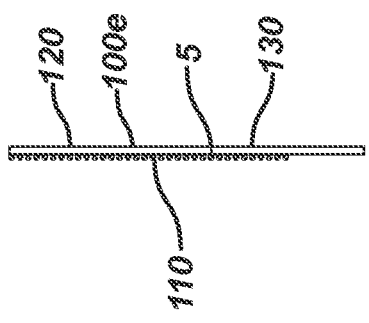
Figure 23:
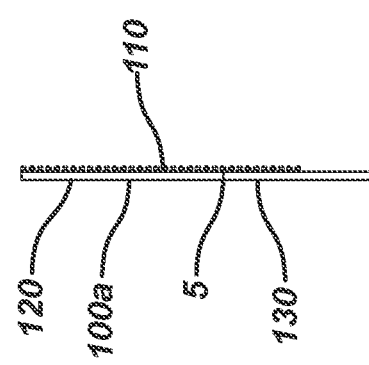
Figure 22:
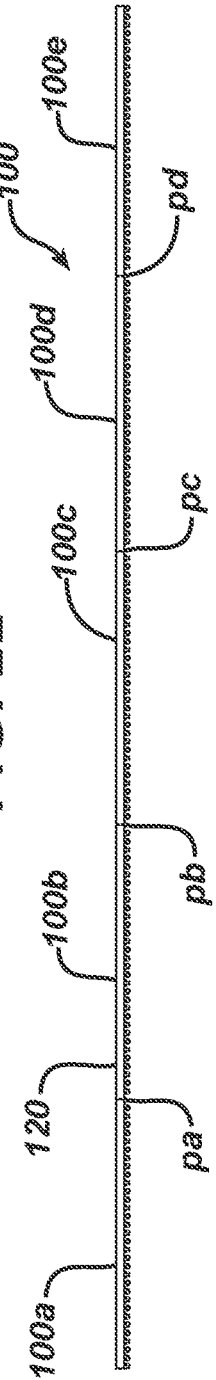
Figure 25:
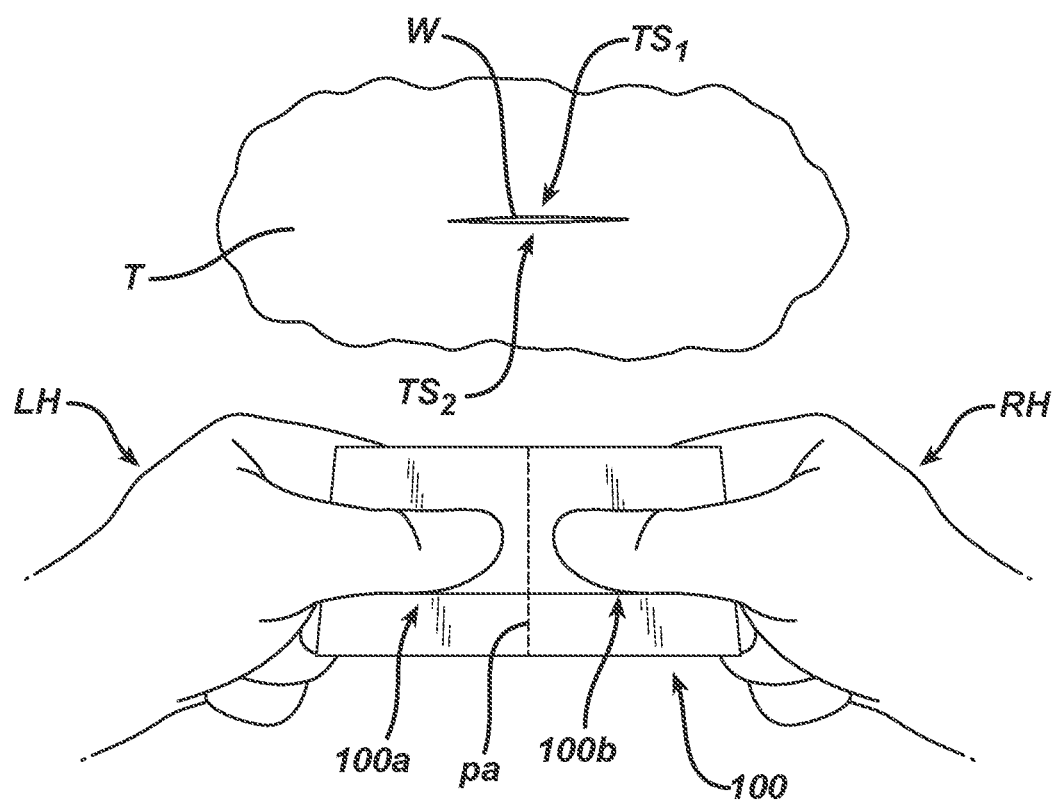
FIG. 25 depicts a first step for use of the device in accordance with the invention.
Figure 26:
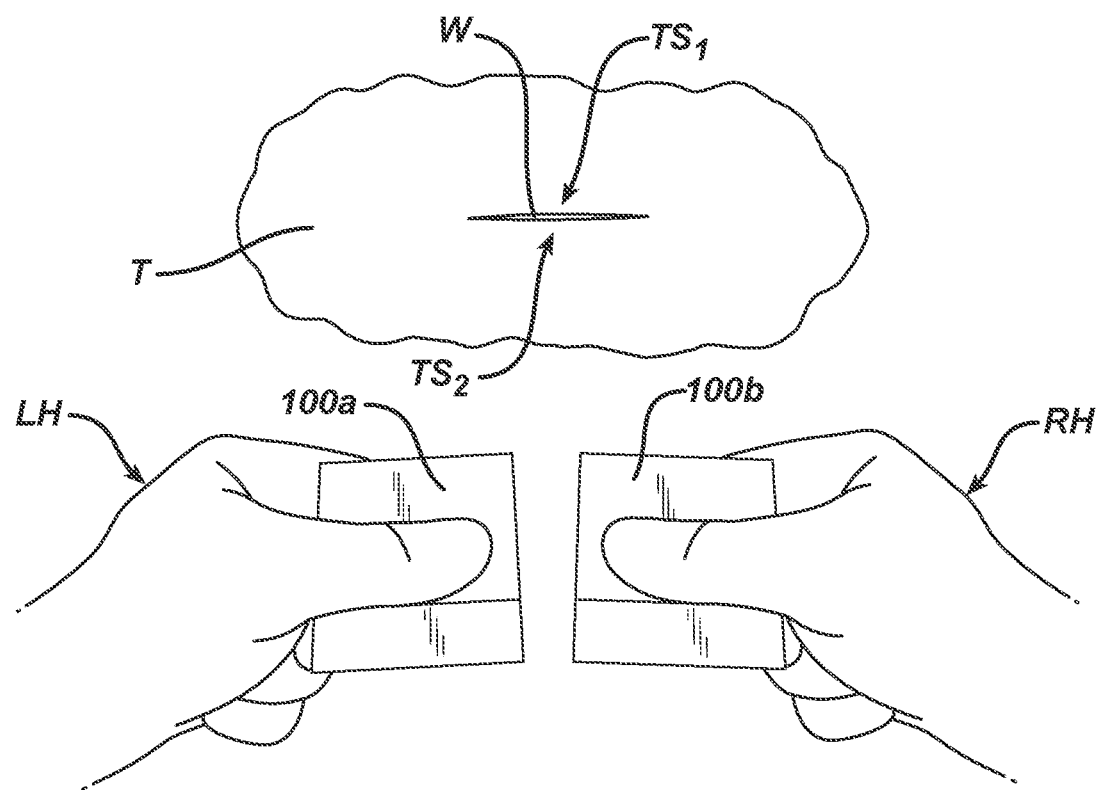
FIG. 26 depicts a second step for use of the device in accordance with the invention.
Figure 27:
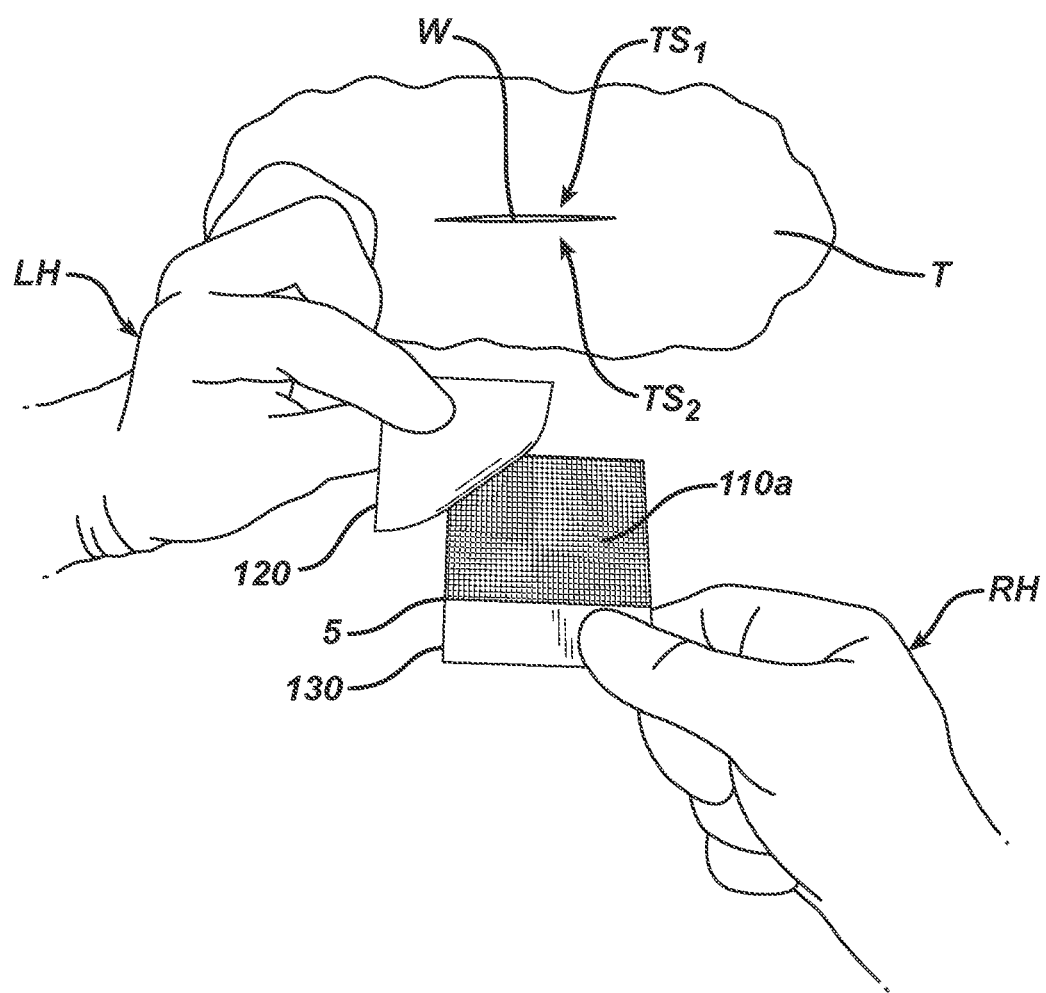
FIG. 27 depicts a third step for use of the device in accordance with the invention.
Figure 28:
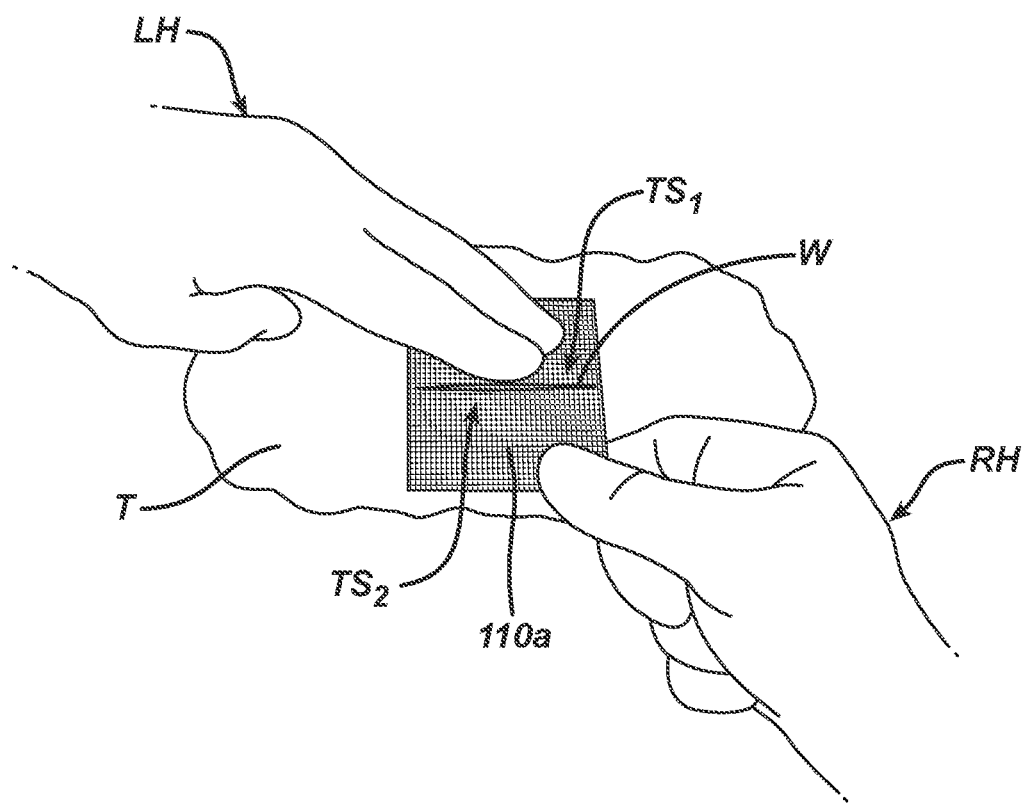
FIG. 28 depicts a fourth step for use of the device in accordance with the invention.
Figure 29:
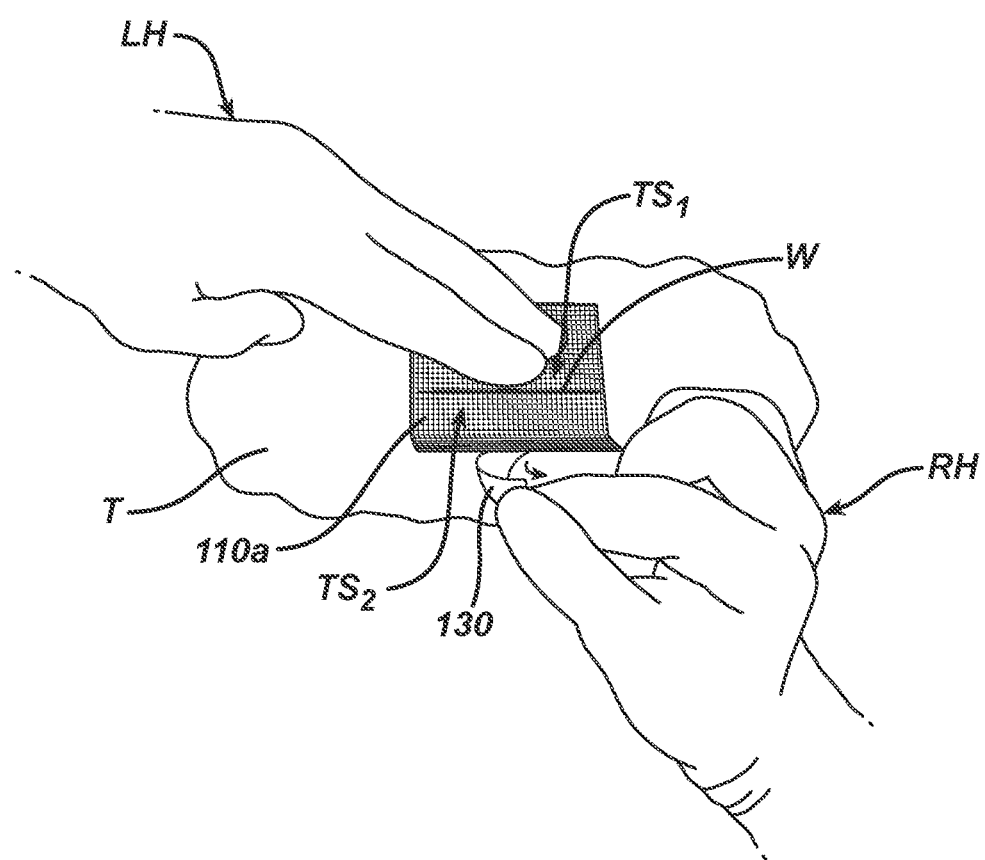
FIG. 29 depicts a fifth step for use of the device in accordance with the invention.

FIG. 14 depicts a top view of the wound closure device 100 of FIG. 12 comprising a non-symmetric, two-part release liner assembly 140 comprising first section 120 of width E and second section 130 of width D separated by cut 5.

FIGS. 15, 16, 17 and 18 depict an upper edge view, a lower edge view, a left-side edge view and a right-side edge view, respectively, of device 100.

Typical and preferred dimensions for wound closure device 100a of FIGS. 13 and 14 are:

| Dimension | Typical (cm) | Preferred range (cm) | Most Preferred (cm) |
| --- | --- | --- | --- |
| A' | 5.0-40.0 | 6.5-25 | 15 |
| A | 1.0-8.0 | 1.5-5 | 3 |
| B | 1.0-10 | 1.5-5 | 3 |
| C | >0.0 | 0.1-2 | 1.0 |
| D | 0.5-4.0 | 0.5-3 | 1.5 |
| E | 0.5-6 | 1-5 | 1.5 |

In general, and particularly referring to device 100a of FIG. 13, device 100a may be of any length A and width B that permits the user to effectively apply to close a wound or incision. Dimension A', the overall length of the multi-segmented device 100, shall vary as a function of the length A varies. For example, for device 100 comprising 5 individual wound closure device segments (i.e., 100a, 100b, 100c, 100d, and 100e), length A' would be five times the length A. For many applications, length A will typically range from about 1 cm to about 8 cm, preferably from about 1.5 cm to about 5 cm, and most preferably about 3 cm. Width B will typically range from about 1.0 cm to about 12 cm, preferably from about 1.5 to about 7 cm, and most preferably about 3.0 cm.

Additionally, wound closure strip 110a may be of any length A that permits the user to effectively apply to close a wound or incision. For many applications, length A will typically range from about 1 cm to about 8 cm, preferably from about 1.5 cm to about 5 cm, and most preferably about 3 cm.

Dimension C, is the distance between the Midline of wound closure device 100a and release liner cut 5 between first section 120 and second section 130. It is dimension C that makes the release assembly a non-symmetric, two-part assembly. If dimension C was equal to 0 cm, then the release assembly would no longer be non-symmetric as then the release assembly cut 5 would be at the Midline and hence the first release section 120 and the second release section 130 would be of equal width. So dimension C should be greater than 0 and preferably ranges from 0.1 cm to about 2 cm and most preferably about 1.0 cm.

Dimension D ranges from 0.5 cm to about 4 cm, preferably from about 0.5 cm to about 3 cm, and most preferably about 1.5 cm. It is within the foregoing ranges that device 100a is conveniently handled with sufficient overlap of wound closure strip 110 and second section 130 to adequately accomplish approximation of the separated topical tissue surface of a wound.

Dimension E is the width of the first section 120 and relates to the width of wound closure strip 110a that is suitable for the user to position and/or reposition wound closure strip 110a for the initial approximation of the separated topical tissue surfaces of a wound. Dimension E ranges from 0.5 cm to about 6 cm, preferably from about 1.0 cm to about 5 cm, and most preferably about 1.5 cm. It is within the foregoing ranges that wound close strip 110a adequately approximates and cover wounds ranging in sizes from 0.25 cm to about 7 cm.

With respect to the various dimensions noted above, one skilled in the art would recognize that other dimensions for the wound closure device of this invention are possible depending on the specific dimensions one skilled in the art may select and adapt to treat wounds or incisions of various sizes and shapes. Additionally, for example, referring to FIG. 13, it is envisioned that wound closure strip 110 (100a) perimeter need not be coextensive with portions of device 100 (100a) perimeter, and can be partially coextensive or not be coextensive at all depending if a margin between wound closure strip 110 and release liner assembly 140 is desired.

For treatment of surgical wound incisions of about 2 cm, a preferred embodiment of device 100a is for an overall length A of about 4 cm and overall width B of about 4.5 cm, wound closure strip 110a of overall length A of about 4 cm and overall width F of about 3.5 cm, Dimension C of about 1.0 cm, Dimension D of about 1.5 cm, Dimension E of about 3.0 cm, Dimension G of about 1.0 cm and Dimension H of about 0.5 cm.

It would be appreciated by one of skill in the art that device 100a may be cut or trimmed to size, or even over layed for wounds within the above identified ranges. In practice, it is desirable to have wound closure strip 110a extend approximately at least 0.3 cm, preferably 1 cm from the longitudinal ends of the wound or incision site. Also as an example of an over lay, it is envisioned that a wound of 7 cm in length may be closed using 3 wound closure strips 100a of 3 cm in length. Over laying multiple wound closure strips 110a provide an advantage of closing wound that may have curvilinear shapes.

FIG. 19 depicts an alternate embodiment of the invention with the bottom view of a wound closure device 100 (prior to separation from the multi-segmented array, removal of the release liners and application to a wound) comprising a non-symmetric, two-part release liner of overall length A' and width. More specifically, segmented devices 110a, 100b, 100c, 100d and 100e are separated by perforations pa, pb, pc, and pd, respectively. Further referring to segmented device 100a, this device of length A and width B comprises top side edge 1, bottom side edge 2, left edge 3 and right edge 4. This embodiment is an example of an instance that wound closure strip 110 perimeter is not coextensive with the perimeter of device 100.

FIG. 20 depicts a top view of the wound closure device 100 of FIG. 19 comprising a non-symmetric, two-part release liner.

FIGS. 21, 22, 23 and 24 depict an upper edge view, a lower edge view, a left-side edge view and a right-side edge view, respectively, of device 100 as depicted in FIGS. 19 and 20.

Typical and preferred dimensions for wound closure device 100a of FIGS. 19 and 20 are:

| Dimension | Typical (cm) | Preferred range | Most Preferred (cm) |
| --- | --- | --- | --- |
| A' | 5.0-40.0 | 6.5-25 | 15 |
| A | 1.0-8.0 | 1.5-5 | 3 |
| B | 1.0-12 | 1.5-7 | 5 |

-continued

| Dimension | Typical (cm) | Preferred range | Most Preferred (cm) |
|---|---|---|---|
| C | >0.0 | 0.1-2 | 1.0 |
| D | 0.5-5 | 0.5-4 | 2 |
| E | 0.5-7 | 1-5 | 3 |
| F | 1.0-8.0 | 1.5-5 | 3 |
| G | 0.25-4.0 | 0.5-2 | 1.0 |
| H | 0.25-4 | 0.5-2 | 1 |

With respect to the various dimensions noted above, one skilled in the art would recognize that other dimensions for the wound closure device of this invention are possible depending on the specific dimensions one skilled in the art may select and adapt to treat wounds or incisions of various sizes and shapes.

In general, device 100a may be of any length A and width B that permits the user to effectively apply to close a wound or incision. Dimension A', the overall length of the multi-segmented device 100, shall vary as a function of the length A varies. For example, for device 100 comprising 5 individual wound closure device segments (i.e., 100a, 100b, 100c, 100d, and 100e), length A' would be five times the length A. For many applications, length A will typically range from about 1 cm to about 8 cm, preferably from about 1.5 cm to about 5 cm, and most preferably about 3 cm. Width B will typically range from about 1.0 cm to about 12 cm, preferably from about 1.5 to about 7 cm, and most preferably about 5 cm.

Additionally, wound closure strip 110a may be of any length A and width F that permits the user to effectively apply to close a wound or incision. For many applications, length A will typically range from about 1 cm to about 8 cm, preferably from about 1.5 cm to about 5 cm, and most preferably about 3 cm. Width F will typically range from about 1.0 cm to about 8 cm, preferably from about 2 cm to about 6 cm, and most preferably about 3.5 cm.

Dimension C, the distance between the Midline of wound closure device 100 and release liner cut 5 between first section 120 and second section 130. It is dimension C that makes the release assembly a non-symmetric, two-part assembly. If dimension C was equal to 0 cm, then the release assembly would no longer be non-symmetric as then the release assembly cut 5 would be at the Midline and hence the first release section 120 and the second release section 130 would be of equal width. So dimension C should be greater than 0 and ranges from 0.1 cm to about 2 cm, preferably from about 0.5 cm to about 1.5 cm, and most preferably about 1.0 cm.

Dimension D ranges from 0.5 cm to about 5 cm, preferably from about 0.5 cm to about 4 cm, and most preferably about 2 cm. It is within the foregoing ranges that device 100 is conveniently handled with sufficient overlap of wound closure strip 110a and second section 130 to adequately accomplish approximation of the separated topical tissue surface of a wound.

Dimension E is the width of the first section 120 and relates to the width of wound closure strip 110a that is suitable for the user to position and/or reposition wound closure strip 110a for the initial approximation of the separated topical tissue surfaces of a wound. Dimension E ranges from 0.5 cm to about 7 cm, preferably from about 1.0 cm to about 5 cm, and most preferably about 3.0 cm. It is within the foregoing ranges that wound close strip 110a adequately approximates and covers wounds ranging in sizes from 0.25 cm to about 7 cm.

Dimension G ranges from 0.25 cm to about 4 cm, preferably from about 0.5 cm to about 2 cm, and most preferably about 1.0 cm. It is within the foregoing ranges that device 100a is conveniently handled without denigrating the pressure sensitive adhesive of the wound-face side of wound closure strip 110a.

Dimension H ranges from 0.25 cm to about 4.0 cm, preferably from about 0.5 cm to about 2.0 cm, and most preferably about 1 cm. It is within the foregoing ranges that device 100a is conveniently handled with sufficient adherence of second section 130 to wound closure strip 110a to accomplish approximation of the wound.

For treatment of surgical wound incisions of about 2 cm, a preferred embodiment of device 100a is for an overall length A of about 4 cm and overall width B of about 4.5 cm, wound closure strip 110a of overall length A of about 4 cm and overall width F of about 3.5 cm, Dimension C of about 1.0 cm, Dimension D of about 1.5 cm, Dimension E of about 3.0 cm, Dimension G of about 1.0 cm and Dimension H of about 0.5 cm.

It would be appreciated by one of skill in the art that device 100a may be cut or trimmed to size, or even over layed for wounds within the above identified ranges. In practice, it is desirable to have wound closure strip 110a extend approximately at least 0.3 cm, preferably 1 cm from the longitudinal ends of the wound or incision site. Also as an example of an over lay, it is envisioned that a wound of 7 cm in length may be closed using 3 wound closure strips 100a of 3 cm in length. Over laying multiple wound closure strips 110a provide an advantage of closing wound that may have curvilinear shapes.

Wound closure strips suitable for use in this invention comprise any suitable strip that is adaptable to close a wound. Preferably, the wound closure strip is porous and will allow a flowable, polymerizable adhesive to permeate the strip and to allow adequate bonding of the strip to a tissue surface being bonded.

The wound closure strip comprises a wound facing side and a top side. The wound facing side further comprises an adhesive such as a pressure sensitive adhesive (PSA) applied over at least a portion of the wound facing side. The adhesive may be provided over the entire wound facing side of the wound closure strip. The PSA is useful for initially approximating the wound. The wound closure strip is preferably porous. By "porous" is meant herein either that the bulk of the wound closure strip has pores, such that subsequently applied polymerizable adhesive composition is soaked up or absorbed by the bulk material, or that the bulk of the wound closure strip has voids (like a net or screen), such that the subsequently applied polymerizable adhesive composition passes directly through the bulk material, with or without being soaked up or absorbed by the bulk material. For example, in the case of textile materials, "porous" is generally used to mean that the applied adhesive composition permeates and passes through interstices between the fibers, but does not necessarily pass into and through the fibers themselves. Preferably the wound closure strip is a mesh.

Such porosity (or other properties such as hydrophobicity or hydrophilicity) will also allow a polymerization initiator or rate modifier to be loaded in or on the wound closure strip prior to use, to initiate the subsequently applied polymerizable adhesive composition. Such porosity will also preferably allow air and fluid to pass through the wound closure strip, either through pores per se, or through voids in the bulk material. Depending upon the degree of porosity and/or the size of the openings, such porosity of the mesh or ability of air and fluid to permeate through the mesh may be tailored either to remain after a final composite material is formed, or to be absent therefrom. The wound closure strip is also preferably non-toxic, as it is intended to be used cover a wound, such as on biological tissues. As such, the wound closure strip should be biologically compatible with the desired substrate (such as tissue, skin, organ, or the like), and is preferably a material that is governmentally approved or generally regarded as safe for the desired purpose. By way of example, suitable wound closure strips are mesh materials and are disclosed in United States Patent Applications 2006/0009099 and 2005/0182443, incorporated herein by reference in their entirety.

Suitable wound closure strip materials may be formed of either synthetic or natural materials. Such material may be formed of either woven or non-woven fabrics or materials. The wound closure strip may be, for example, any suitable polymeric film, plastic foam (including open celled foam), a woven fabric, knitted fabric, a non-woven fabric, mixture thereof, or the like.

In particular, suitable wound closure strips may thus be prepared, for example, from nylon, a polyolefin film, such as polyethylene, polypropylene, ethylene propylene copolymers, and ethylene butylene copolymers, polyurethanes, polyurethane foams, polystyrenes, plasticized polyvinylchlorides, polyesters, polyamides, polylactic acid, polyglycolic acid, polycaprolactone, copolymer mixtures of the above, and cotton. Suitable specific examples include, for example, nylon, polyethylene, polypropylene, ethylene propylene copolymers, ethylene butylene copolymers, polyurethane, polystyrene, plasticized polyvinylchloride, polyester, polyamide, cotton, polytetrafluoroethylene (PTFE), biovascular material, collagen, Gore-Tex®, DACRON®, etc.

The wound closure strip may be formed of a synthetic, semi-synthetic, or natural organic material. Thus, for example, the wound closure strip may be formed of a synthetic or natural polymer material, but not from a material such as metal (such as silver, steel or the like) or glass or ceramic. The wound closure strip may be either biodegradable, or not biodegradable. The wound closure strip is preferably resistant to tearing.

The thickness of the wound closure strip may be from about 0.05 mm to about 10 mm. In another embodiment, the thickness of the wound closure strip is from about 0.1 mm to about 7 mm, preferably from about 0.3 mm to about 5 mm, most preferably from about 0.3 mm to about 3 mm.

The wound closure strip may be selected to be elastic or have some memory effect. In such embodiments, the elastic properties of the mesh may desirably provide a degree of pressure or stress at the application site, for example, to maintain wound edge approximation. Likewise, in embodiments where such additional degree of pressure or stress at the application site is not desired, the mesh may be selected to have less or no elasticity.

The wound closure strip may be either biodegradable, or not biodegradable. By "biodegradable" is meant that the mesh biodegrades over time in vivo, such that it does not require physical removal of the mesh after a set period of time. Thus, for example, a biodegradable mesh is one that, in the in vivo environment, will biodegrade over a period of from about one week to about five years. A non biodegradable material is one that does not biodegrade in an in vivo environment within about five years. Such a non biodegradable material thus would require physical removal of the wound closure strip at a desired time, rather than slowly deteriorating over time or may slough off naturally from the tissue.

The wound closure strip preferably includes one or more chemical materials located in or on it. For example, one or more chemical substances may be dispersed in or on the wound closure strip, such as being chemically bound, physically bound, absorbed, or adsorbed to it. Thus, for example, the wound closure strip preferably includes at least a polymerization initiator or rate modifier, and may optionally include one or more bioactive materials. As desired, the one or more chemical substances may be either immobilized in or on the wound closure strip, for example, so that it has a desired effect but is not detached from the wound closure strip during use.

For example, a polymerization initiator or rate modifier may be loaded in or on the wound closure strip so that the initiator or rate modifier provides the desired initiation or rate modification effect to a subsequently applied polymerizable adhesive composition. The polymerization initiator or rate modifier may be immobilized in or on the wound closure strip, so that the initiator or rate modifier does not become detached from the wound closure strip and its residues are dispersed in the resultant polymeric material. Alternatively, for example, the polymerization initiator or rate modifier may be initially attached to the wound closure strip, but only in such a manner that it becomes mobilized or solubilized by a subsequently applied polymerizable adhesive composition and dispersed in the resultant polymeric material.

If desired, a combination of chemical substances may also be provided in or on the wound closure strip, to provide multiple effects. For example, as described above, a first chemical species (such as a polymerization initiator or rate modifier) may be immobilized in or on the wound closure strip, while a second, different chemical species (such as a bioactive material) may be detachably attached to the wound closure strip. Other combinations of chemical species and resultant effects are also envisioned.

The chemical substance may be applied in a uniform manner to the wound closure strip, such that there is a substantially uniform concentration of the chemical substance across the wound closure strip. Alternatively, the chemical substance may be applied such that a concentration gradient exists across or through the wound closure strip. For example, a greater or smaller concentration of the chemical substance could exist at the center or edges of the wound closure strip, or a greater or smaller concentration of the chemical substance could be applied on one side of the wound closure strip as compared to an opposite side. Further, the chemical substance may be applied in a uniform manner to the wound closure strip, or it may be applied in a non-uniform random or patterned manner (such as lines, dots, concentric circles, or the like). The chemical substances may also be on, beneath, or in the adhesive layer applied to the wound closure strip.

When present in or on the wound closure strip, the chemical substances (i.e., polymerization initiator, rate modifier, and/or bioactive materials, or other additives), may be incorporated in or on the wound closure strip in any suitable manner. For example, the chemical substance may be wound closure strip added to the wound closure strip by contacting the wound closure strip with a solution, mixture, or the like including the chemical substances. The chemical substance may be added to the wound closure strip, for example, by dipping, spraying, roll coating, gravure coating, brushing, vapor deposition, or the like. Alternatively, the chemical substance may be incorporated into or onto the wound closure strip during manufacture of the wound closure strip, such as during molding, knitting/weaving, scouring, tenting, plaiting or other processing or the like of the wound closure strip.

Other chemical substances that may be present in or on the wound closure strip include, but are not limited to, any suitable and preferably compatible additive that enhances performance of the composite structure. Such additional chemical substances may be bioactive or non-bioactive. Suitable other chemical substances thus include, but are not limited to, colorants (such as inks, dyes and pigments), scents, protective coatings that do not chemically detach, temperature sensitive agents, drugs, wound-healing agents, anti-microbial agents and the like.

The polymerization initiator or rate modifier loaded in or on the wound closure strip may provide a number of advantages for example, the tailoring of the setting or polymerization time of the applied polymerizable adhesive composition. For example, the type and/or concentration of initiator that is applied to the wound closure strip may be selected so as to provide faster or slower polymerization time. The concentration of polymerization initiator or rate modifier may be increased to provide a faster polymerization time, or may be decreased to provide a slower polymerization time.

Because the polymerization initiator or rate modifier is loaded directly in or on the wound closure strip, it is not necessary to mix the polymerizable adhesive composition with a polymerization initiator or rate modifier prior to application. This may allow a longer working time, where the polymerizable monomer composition may be more precisely and carefully applied over a longer period of time.

Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfate, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics. The polymerization initiator, accelerator, rate-modifier, and/or cross-linking agent may be incorporated into the mesh using impregnation methods known in the art.

The two-part release liner assembly is a backing film comprising individually peelable sections. The first section 120 is coextensive with at least a portion of wound closure strip 110 and is of larger width compared to the second section 130. Second section 130 comprises at least a portion that is not coextensive with the wound closure strip 110. This non-coextensive portion of section 130 permits manipulation and placement of wound closure strip 110 without disturbing or denigrating the pressure sensitive adhesive contained on the wound-facing side of wound closure strip 110. In some instances, it is contemplated that second section 130 may be wider than first section 120 to aid in manipulation and gripping of the wound closure device as the separated topical tissue surfaces are being approximated.

The material for the invention's release liner assembly may be any suitable backing or release material used to cover the adhesive substances applied to the wound facing side of the wound closure strip. Such backing materials are well known in the art for covering adhesives and can include, for example, paper, plastic, or the like. By way of example, the release liner assembly may be a silicone treated material. Preferably, the release liner assembly is of a material that prevents or eliminates the wound closure strip from sticking to itself.

The method of wound closure or tissue bonding herein disclosed includes a polymerizable adhesive composition applied over the wound closure strip after the wound closure strip is applied to a tissue or wound site. The polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable α-cyanoacrylate monomers which may be used, alone or in combination, include alkyl α-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other α-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl α-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

The wound closure device herein disclosed may be provided in a kit comprising additional components. The kit may comprise at least one wound closure strip as herein described, and one or more containers of polymerizable adhesive composition. The different components or groups of components may be sterilized in separate containers before packaging the components or groups of components within a kit, and thereafter sterilizing the kit as disclosed in co-assigned U.S. Pre-grant Patent Publication No. 2004/0120849, incorporated herein by reference in its entirety.

The adhesive substance used on the wound closure strip may, for example, be any suitable adhesive substance. Preferably, the adhesive substance is a medical grade adhesive, such as acrylic based pressure sensitive adhesives (PSAs), rubber based pressure sensitive adhesives, silicone pressure sensitive adhesives, mixtures thereof, or the like. It is preferred that the adhesive substance be different from the polymerizable adhesive composition. Thus, for example, it is preferred that while the polymerizable adhesive composition can be, for example, a polymerizable monomeric adhesive composition, the adhesive substance is a material that is not a polymerizable adhesive composition, such as a pressure sensitive adhesive.

Suitable rubber based PSAs include, but are not limited to, those taught in U.S. Pat. No. 5,705,551 and in U.S. Pat. No. 4,080,348, the disclosures of which are hereby incorporated by reference. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

A particularly useful rubber based adhesive is that which has a thermoplastic elastomeric component and a resin component. The thermoplastic elastomeric component contains about 55-85 parts of a simple A-B block copolymer wherein the A-blocks are derived from styrene homologs and the B-blocks are derived from isoprene, and about 15-45 parts of a linear or radical A-B-A block copolymer wherein the A-blocks are derived from styrene or styrene homologs and the B-blocks are derived from conjugated dienes or lower alkenes, the A-blocks in the A-B block copolymer constituting about 10-18 percent by weight of the A-B copolymer and the total A-B and A-B-A copolymers containing about 20 percent or less styrene. The resin component consists of essentially of tackifier resins for the elastomeric component. In general, any compatible conventional tackifier resin or mixture of such resins may be used. These include hydrocarbon resins, rosin and rosin derivatives, polyterpenes and other tackifiers. The adhesive substance may contain about 20-300 parts of the resin component per one hundred parts by weight of the thermoplastic elastomeric component. One such rubber based adhesive substance is commercially available from Ato Findley under the trade name HM3210.

Useful acrylic based PSAs include, but are not limited to, those taught in U.S. Pat. Nos. 5,947,917 and 5,164,444 (acrylic emulsion), U.S. Pat. No. 5,623,011 (tackified acrylic emulsion). It can also be radiation curable mixture of monomers with initiators and other ingredients such as those taught in U.S. Pat. No. 5,232,958 (UV cured acrylic) and U.S. Pat. No. 5,232,958 (EB cured). The disclosures of these patents are hereby incorporated by reference.

It is contemplated that any acrylic based polymer capable of forming an adhesive layer with sufficient tack to adhere to the wound closure strip, the backing film or to a substrate, and with acceptable adhesion to skin, may be used. In certain embodiments, the acrylic polymers for the pressure-sensitive adhesive layers include those formed from polymerization of at least one alkyl acrylate monomer or methacrylate, an unsaturated carboxylic acid and optionally a vinyl lactam. Examples of suitable alkyl acrylate or methacrylate esters include, but are not limited to, butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and the like, and mixtures thereof. Examples of suitable ethylenically unsaturated carboxylic acids include, but are not limited to, acrylic acid, methacrylic acid, fumaric acid, itaconic acid, and the like, and mixtures thereof. A preferred ethylenically unsaturated carboxylic acid monomer is acrylic acid. Examples of suitable vinyl lactams include, but are not limited to, N-vinyl caprolactam, 1-vinyl-2-piperidone, 1-vinyl-5-methyl-2-pyrrolidone-, vinyl pyrrolidone, and the like, and mixtures thereof.

Useful silicone pressure sensitive adhesives include those commercially available from Dow Corning Corp., Medical Products and those available from General Electric. Examples of silicone adhesives available from Dow Corning include those sold under the trademarks BIO-PSA X7-3027, BIO-PSA X7-4919, BIO-PSA X7-2685, BIO-PSA X7-3122 and BIO-PSA X7-4502. Additional examples of silicone pressure sensitive adhesives are described in U.S. Pat. Nos. 4,591,622, 4,584,355, 4,585,836 and 4,655,767, the entire disclosures of which are incorporated herein by reference.

The adhesive substance may also include one or more tackifiers, plasticizers, antioxidants, cutting agents such as waxes, and surfactants. Other optional materials that may be added to the adhesive substance layer in minor amounts (typically less than about 25% by weight of the elastomeric phase) include pH controllers, medicaments, bactericides, growth factors, wound healing components such as collagen, antioxidants, deodorants, perfumes, antimicrobials and fungicides.

FIGS. 7 to 11 depict steps for the use of the device of this invention.

Figure 10:
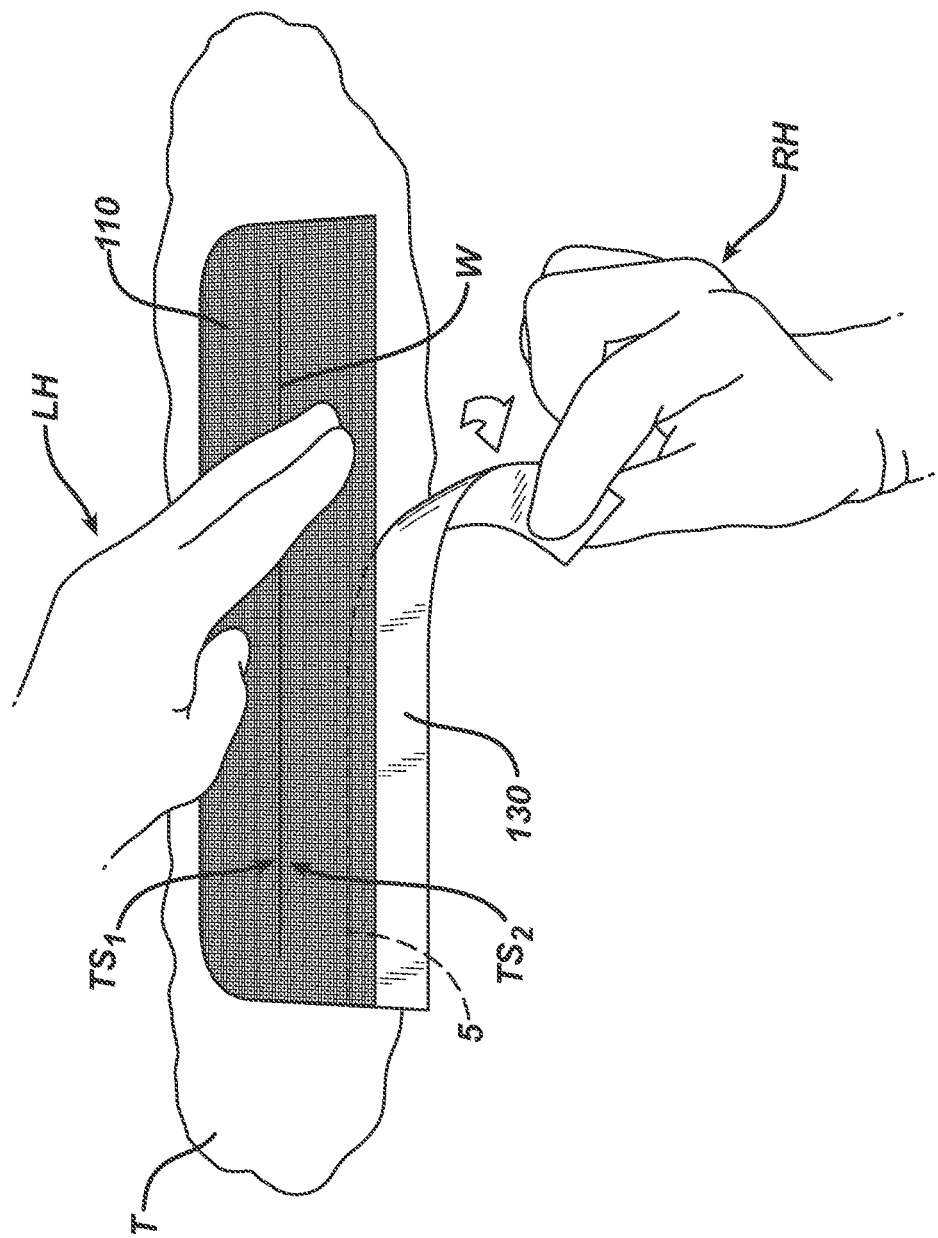
FIG. 10 depicts a fourth step for use of the device in accordance with the invention.
Figure 11:
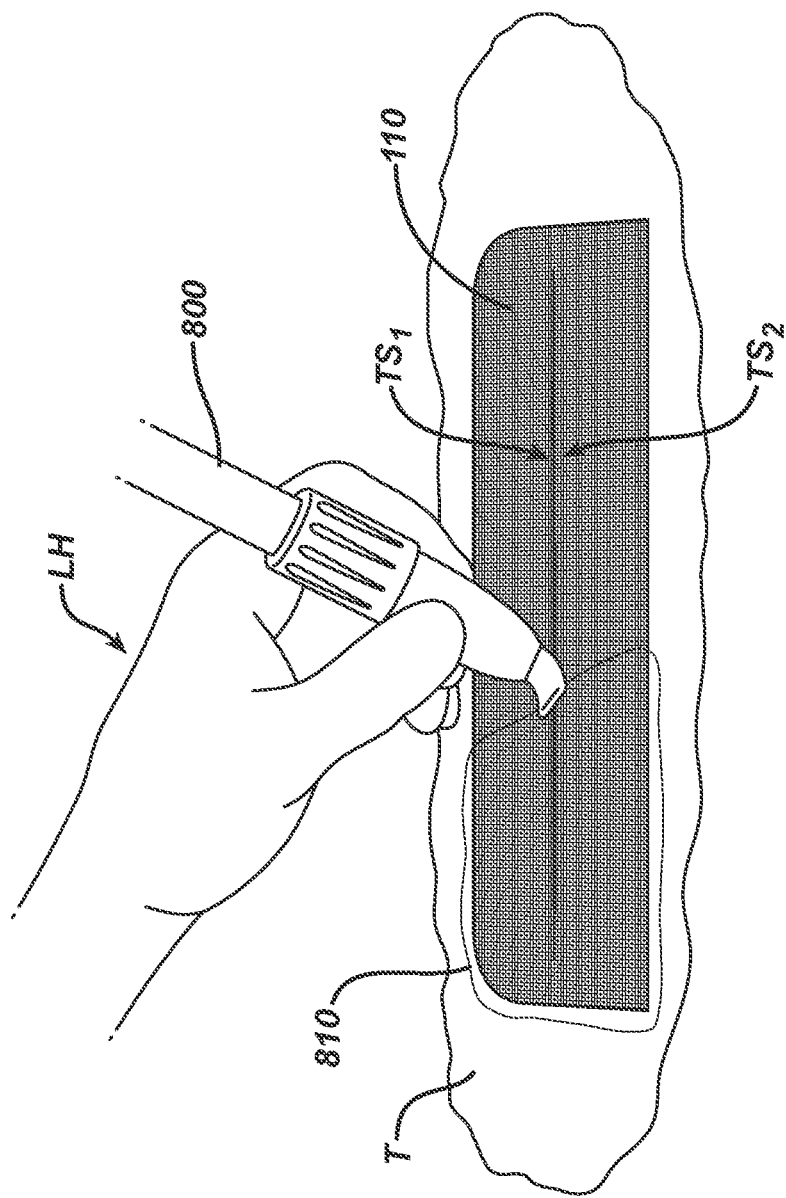
FIG. 11 depicts a fifth step for use of the device in accordance with the invention.

In particular and referring to FIG. 7, once a suitable wound W has been identified for closure of tissue T by joining topical tissue surface $TS_1$ with topical tissue surface $TS_2$, first section 120 of wound closure device 100 is removed by grasping and pulling section 120 (for example, with left hand, LH) while holding second section 130 (for example with right hand RH) to separate first section 120 from wound closure strip 110. Next, FIG. 8 illustrates the device being positioned axially along a side of wound W of tissue T and contacting a first separated topical tissue surface TS$_1$. FIG. 9 depicts tissue surface TS$_1$ on one side of wound W being pulled to approximate a second separated topical tissue surface TS$_2$ of wound W to the first separated topical tissue surface TS$_1$ of wound W by pulling second section 130. FIG. 10 shows second section 130 being removed from wound closure strip 110 and wound closure strip 110 being more firmly secured to topical tissue surface TS$_2$ by the user. Once wound closure strip 110 is firmly contacting tissue T and has approximated TS$_1$ to TS$_2$ of wound W, FIG. 11 illustrates application of a suitable flowable, polymerizable adhesive being applied from applicator 800 which permeates wound closure strip 110 to form film 810.

Figure 30:
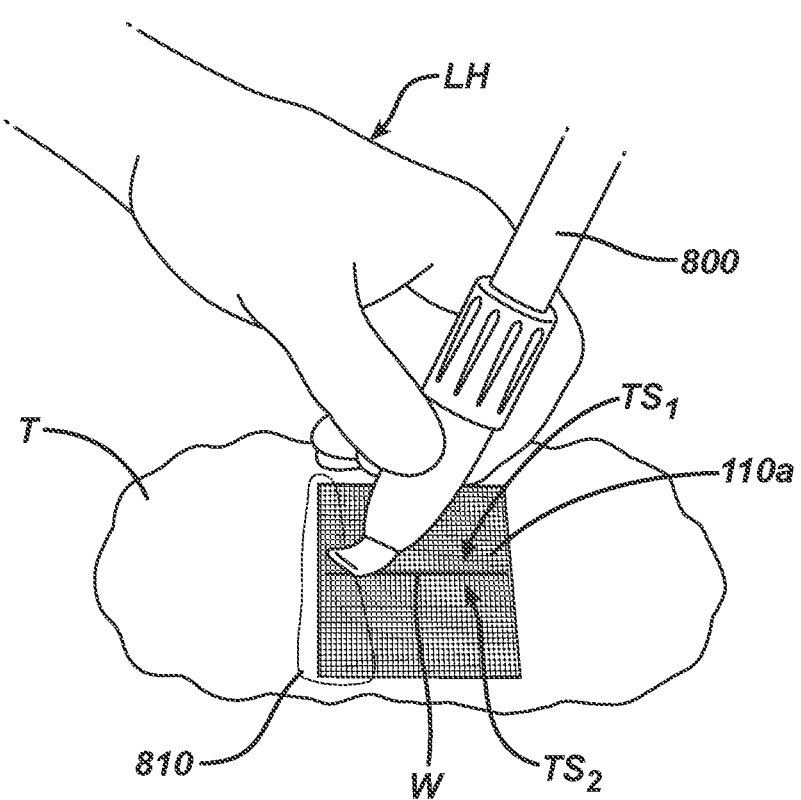
FIG. 30 depicts a sixth step for use of the device in accordance with the invention.

FIGS. 25-30 depict typical steps used in a method of applying a segment of the multi-segmented device embodiment to wound W of tissue T by joining topical tissue surface TS$_1$ with topical tissue surface TS$_2$. Referring to these figures, the user accomplishes the method for the closing of a wound comprising the steps of:

a) grasping multi-segmented device 100; (FIG. 25)
b) separating segment 100a from device 100; (FIG. 26)
c) removing first section 120 of release liner 140 from device 100a to expose wound closure strip 110a coated with a pressure sensitive adhesive; (FIG. 27)
d) positioning wound closure strip 110 axially along a side of wound W of tissue T and contacting a first separated topical tissue surface TS$_1$ and pulling wound closure strip 110 across wound W to approximate and join topical tissue surface TS$_1$ with topical tissue surface TS$_2$; (FIG. 28)
e) removing second section 130 of release liner 140; (FIG. 29) and
f) optionally applying a polymerizable liquid adhesive from applicator 800 to form film 810 over wound closure strip 110. (FIG. 30)

Advantages of the methods, devices and systems of this invention include: clear visualization for placement of wound closure strip 110 to approximate wound W by abutting the separate topical tissue surfaces of wound W; flexibility to reposition wound closure strip 110 and adjust the approximation of wound W (i.e., the abutment of the separated topical tissue surfaces of the W) before wound closure strip 110 is fully placed on the abutted topical tissue surfaces; ability to handle placement of wound closure strip 110 without denigrating or minimizing denigration of the adhesive side of wound closure strip 110; manipulation of wound closure strip 110 is more stable during tissue approximation as second section 130 provides rigidity for wound closure strip 110.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A wound closure device having a length A, a width B, an upper edge, a lower edge, a right-hand edge, and a left-hand edge comprising:
    a wound closure strip having a length A, a width F, a wound-facing side, a top side, an upper edge and a lower edge, the wound-facing side comprising an adhesive applied over at least a portion of the wound facing side;
    a release liner assembly detachably adhered to the wound closure strip by the adhesive, the release liner assembly consisting of a first section having a length A and a width E and a second section having a length A and a width D;
    wherein the release liner assembly extends the full length A of the wound closure device and extends the full width B of the wound closure device;
    wherein the width F of the wound closure strip is greater than the width E of the first section but less than the full width B of the wound closure device; and
    wherein the first section and the second section are separated from each other by a liner cut.

2. The wound closure device according to claim 1, wherein the wound closure strip is a mesh.

3. The wound closure device according to claim 1, wherein the adhesive is provided over the entire wound-facing side of the wound closure strip.

4. The wound closure device according to claim 1, wherein the adhesive is a medical grade adhesive selected from acrylic based pressure sensitive adhesives (PSAs), rubber based pressure sensitive adhesives, silicone pressure sensitive adhesives and mixtures thereof.

5. The wound closure device of claim 1 wherein the wound closure strip includes at least a polymerization initiator or rate modifier.

6. A kit comprising:
    (a) the wound closure device of claim 1; and
    (b) a polymerizable adhesive composition for application over the wound closure strip after the wound closure strip has been applied to a tissue or wound site.

7. The kit according to claim 6, wherein the polymerizable adhesive composition is different from the adhesive applied to the wound facing side of the wound closure strip.

8. A method of closing a wound having at least a first separated topical tissue surface and a second separated topical tissue surface comprising the steps of:
    a) utilizing the device of claim 1;
    b) removing the first section of the release liner assembly to expose a portion of the wound facing side of the wound closure strip while grasping a tab of the second section of the release liner assembly;
    c) adhering a portion of the exposed wound facing side of the wound closure strip to the at least first separated topical tissue surface and pulling the tab of the second section of the release liner toward the at least second separated topical tissue surface to form two abutted topical tissue surfaces and further adhering the exposed wound facing side of the wound closure strip to the at least second topical tissue surface; and
    d) removing the second section of the release liner assembly to further expose a wound facing side of the wound closure strip and adhering the further exposed wound closure strip the second topical tissue surface.

9. The method of claim 8, further comprising the step of applying a flowable, polymerizable adhesive over the wound closure strip.

10. The method of claim 9, wherein the wound closure strip comprises a mesh.

11. The method of claim 10, when the mesh comprises materials selected from the group consisting of polyesters, polyolefins and polyamides.

12. The method of claim 11, wherein the flowable, polymerizable adhesive comprises a polymerizable 1,1-disubstituted ethylene monomer.

13. The method of claim 12, wherein the flowable, polymerizable adhesive comprises an α-cyanoacrylate monomer.

14. The method of claim 13, wherein the mesh further comprises an initiator.

15. The method of claim 14, wherein the initiator is selected from the group consisting of benzalkonium and benzyltrialkyl ammonium halides.

16. The method of claim 15 wherein the initiator is benzalkonium chloride.

17. The method of claim 16 wherein the adhesive is an acrylic based pressure sensitive adhesive.

* * * * *